United States Patent
Boone et al.

(10) Patent No.: US 7,516,872 B2
(45) Date of Patent: Apr. 14, 2009

(54) APPLICATORS, DISPENSERS AND METHODS FOR MIXING, DISPENSING AND APPLYING ADHESIVE OR SEALANT MATERIAL AND ANOTHER MATERIAL

(75) Inventors: Eric J. Boone, St. Michael, MN (US);
Keith R. D'Alessio, Cary, NC (US);
John F. Goodman, Ann Arbor, MI (US);
Scott A. Keplinger, Raleigh, NC (US);
Anthony S. Voiers, Raleigh, NC (US);
Daniel J. Tomko, Wake Forest, NC (US); William F. Johnson, Jr., Wake Forest, NC (US)

(73) Assignee: Closure Medical Corp., Raleigh, NC (US)

( * ) Notice: Subject to any disclaimer, the term of this patent is extended or adjusted under 35 U.S.C. 154(b) by 398 days.

(21) Appl. No.: 10/933,463

(22) Filed: Sep. 3, 2004

(65) Prior Publication Data

US 2006/0049203 A1    Mar. 9, 2006

(51) Int. Cl.
*B67D 5/00* (2006.01)
*B67D 5/60* (2006.01)
*B65D 35/22* (2006.01)
*B65D 35/28* (2006.01)
*B65D 88/54* (2006.01)
*B65D 83/04* (2006.01)
*A61L 2/04* (2006.01)
*B43K 5/14* (2006.01)

(52) U.S. Cl. ............ 222/212; 222/80; 222/94; 222/95; 222/325; 222/145.5; 222/145.8; 206/532; 422/294; 401/134

(58) Field of Classification Search ............ 222/80, 222/94, 95, 105, 207, 209, 212, 145.7, 145.5, 222/325, 145.8, 153.13; 422/294; 401/132–134; 206/532
See application file for complete search history.

(56) References Cited

U.S. PATENT DOCUMENTS

| D145,586 | S |   | 9/1946 | Reynolds |
|---|---|---|---|---|
| D155,031 | S |   | 8/1949 | Patterson |
| 3,797,488 | A |   | 3/1974 | Hurschman et al. |
| 4,543,005 | A |   | 9/1985 | Kuboshima |
| 4,581,021 | A |   | 4/1986 | Landau et al. |
| 4,640,637 | A |   | 2/1987 | Winthrop |
| 4,784,506 | A | * | 11/1988 | Koreska et al. ............ 401/132 |
| 4,813,870 | A |   | 3/1989 | Pitzen et al. |
| 4,960,340 | A |   | 10/1990 | Tamiya et al. |
| 5,171,149 | A |   | 12/1992 | Alpert |
| 5,193,928 | A |   | 3/1993 | Blazer et al. |

(Continued)

OTHER PUBLICATIONS

U.S. Appl. No. 09/430,177, filed Oct. 29, 1999, Narang et al.

*Primary Examiner*—Kevin P Shaver
*Assistant Examiner*—Melvin A Cartagena

(57) ABSTRACT

An applicator/dispenser for dispensing, mixing and/or applying a polymerizable monomeric adhesive or sealant material comprises: a body portion; an actuator movable relative to the body portion; a cavity in the body portion; and a piercing or breaking portion on the actuator. Movement of the actuator relative to the body portion moves the piercing or breaking portion into the cavity. When a container of adhesive or sealant material is at least partially disposed within the cavity, movement of the actuator relative to the body portion moves the piercing or breaking portion to rupture the container for mixing, dispensing and/or applying the adhesive or sealant material.

61 Claims, 25 Drawing Sheets

U.S. PATENT DOCUMENTS

| | | | |
|---|---|---|---|
| 5,302,358 A * | 4/1994 | Andersen et al. ............ 422/305 |
| 5,308,180 A | 5/1994 | Pournoor et al. |
| 5,358,349 A | 10/1994 | Burroughs et al. |
| 5,445,462 A | 8/1995 | Johnson et al. |
| 5,658,084 A | 8/1997 | Wirt |
| 5,791,801 A | 8/1998 | Miller |
| 5,909,828 A * | 6/1999 | Salisbury ................... 222/103 |
| 5,928,611 A | 7/1999 | Leung |
| 6,099,807 A | 8/2000 | Leung |
| D443,303 S | 6/2001 | Ashe |
| 6,283,933 B1 | 9/2001 | D'Alessio et al. |
| 6,328,715 B1 | 12/2001 | Dragan et al. |
| 6,340,097 B1 | 1/2002 | D'Alessio et al. |
| 6,371,675 B1 | 4/2002 | Hoang et al. |
| 6,372,313 B1 * | 4/2002 | D'Alessio et al. .......... 428/34.1 |
| 6,425,704 B2 | 7/2002 | Voiers et al. |
| 6,447,476 B1 | 9/2002 | Sogaro |
| 6,478,191 B1 | 11/2002 | D'Alessio et al. |
| D471,586 S | 3/2003 | Geiselhart et al. |
| 6,536,975 B1 | 3/2003 | Tufts |
| D472,578 S | 4/2003 | Plantz et al. |
| 6,547,467 B2 | 4/2003 | Quintero |
| 6,595,940 B1 | 7/2003 | D'Alessio et al. |
| 6,705,790 B2 | 3/2004 | Quintero et al. |
| 6,915,901 B2 | 7/2005 | Feinberg et al. |
| 7,306,390 B2 * | 12/2007 | Quintero et al. ............. 401/133 |
| 2001/0031170 A1 | 10/2001 | Voiers et al. |
| 2002/0076255 A1 | 6/2002 | Hoang et al. |
| 2002/0108875 A1 | 8/2002 | Feinberg et al. |
| 2003/0060746 A1 | 3/2003 | Mark |
| 2003/0063944 A1 | 4/2003 | Leung |
| 2003/0077386 A1 | 4/2003 | Azevedo |
| 2003/0080151 A1 | 5/2003 | D'Alessio et al. |
| 2003/0186005 A1 | 10/2003 | Rivera et al. |

* cited by examiner

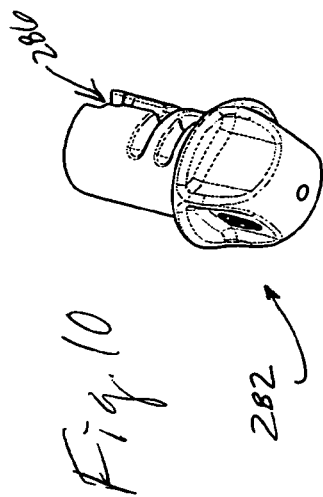
Fig. 10
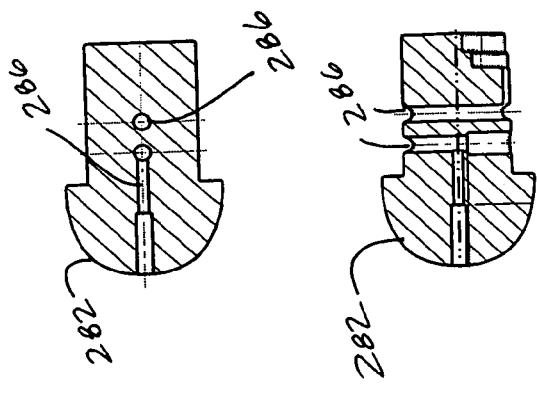
Fig. 11
Fig. 12
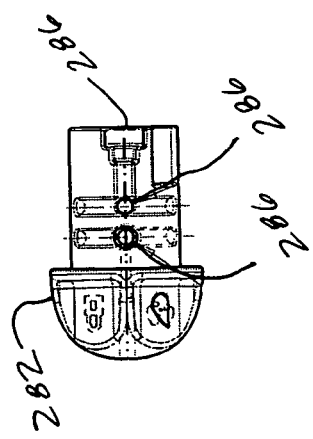
Fig. 13

APPLICATORS, DISPENSERS AND METHODS FOR MIXING, DISPENSING AND APPLYING ADHESIVE OR SEALANT MATERIAL AND ANOTHER MATERIAL

BACKGROUND OF THE INVENTION

This invention relates to applicators and/or dispensers for mixing, dispensing and/or applying an adhesive or sealant material, for example, a polymerizable monomer compound such as a cyanoacrylate adhesive or sealant, along with another material, for example, a polymerization rate modifier such as an initiator, particularly for medical use.

Numerous swabs, applicators, dispensers and kits for dispensing and applying various materials, including adhesive or sealant materials, are known. However, these known arrangements possess various shortcomings that make them undesirable in many applications.

Monomer and polymer adhesives or sealants are used in both industrial (including household) and medical applications. Included among these adhesives or sealants are the 1,1-disubstituted ethylene monomers and polymers, such as the α-cyanoacrylates. Since the discovery of the adhesive or sealant properties of such monomers and polymers, they have found wide use due to the speed with which they cure, the strength of the resulting bond formed, and their relative ease of use. These characteristics have made the α-cyanoacrylate adhesives or sealants the primary choice for numerous applications such as bonding plastics, rubbers, glass, metals, wood, and, more recently, biological tissues.

Medical applications of 1,1-disubstituted ethylene monomer adhesive or sealant compositions include use as an alternate or an adjunct to surgical sutures and staples in wound closure as well as for covering and protecting tissue wounds such as lacerations, abrasions, burns, stomatitis, sores, and other open surface wounds. When such an adhesive or sealant is applied, it is usually applied in its monomeric form, and the resultant polymerization gives rise to the desired adhesive or sealant bond.

Applicators for dispensing a polymerizable and/or crosslinkable material, such as a 1,1-disubstituted ethylene formulation, are disclosed in U.S. Pat. No. 5,928,611 to Leung and copending U.S. patent application Ser. No. 09/430,177, filed Oct. 29, 1999. In general, many different 1,1-disubstituted ethylene formulations are known for various applications, for example, cyanoacrylate formulations used as fast-acting surgical adhesive or sealants, bioactive agent release matrixes and implants utilized in medical, surgical and other in vivo applications. Such formulations include those disclosed by Leung and the references cited therein.

However, due to the need to apply the adhesive or sealant in its monomeric form, and due to the rapid polymerization rate of the monomers, it has been very difficult to design effective and commercially viable applicators and/or dispensers. Such applicators and/or dispensers must counterbalance the competing requirements that the monomer not prematurely polymerize, that the monomer be easily applied, that the monomer polymerize at a desired rate upon application, and that the sanitary and/or sterile properties of the monomer and applicator—whether real or perceived—be maintained. This latter requirement, that the actual or perceived sanitary and sterile condition of the monomer and applicator be maintained, is particularly important in medical applications, where the user and/or the patient desires a clean product so as not to introduce further bacteria or foreign matter into a wound site.

A further problem in addressing the above requirements of adhesive or sealant applicators and/or dispensers is the need to provide a stable monomer product. Particularly in small quantities, cyanoacrylate monomers are prone to premature polymerization, which would render the product useless. Thus, industrial production of monomeric adhesive or sealant compositions has had to balance rapid cure rates and high bond strengths with shelf-life. The shelf-life of these adhesives or sealants is primarily related to stability (i.e., constancy of compositional nature), uncured physical properties, rate of cure of the adhesive or sealant, as well as final cured properties of the composition. For example, the shelf-life of a monomeric α-cyanoacrylate composition may be measured as a function of the amount of time the composition can be stored before unacceptable levels of polymerization, such as measured by viscosity increase, occur. Unacceptable levels are indicated by a level of polymerization product that reduces the usefulness of the composition in the application for which it is produced.

Additional problems with known applicators and/or dispensers include, for example, the adhesive or sealant being fed from the applicator/dispenser by gravity only. Such gravity feed methods do not allow for desired control over the flow of the adhesive or sealant from the applicator/dispenser during use. Furthermore, known applicators/dispensers do not allow for fine control over and placement of the adhesive or sealant at the time of use.

Known devices fail to provide an applicator and/or dispenser that is optimized for convenient dispensing and application of adhesive or sealant materials on a variety of surfaces and structures. The known applicators are generally either optimized for delivery of other compositions or are inconvenient for use in conjunction with adhesives or sealants. Furthermore, such conventional devices generally do not address the competing needs of ease of use and adhesive or sealant stability prior to application.

SUMMARY OF THE INVENTION

This invention addresses the above needs by providing applicators and dispensers that permit economical and efficient use of adhesive or sealant compositions. In embodiments of this invention, applicators and/or dispensers are provided that are more user friendly. In embodiments of this invention, applicators and/or dispensers are provided that are more ergonomic. In embodiments of this invention, applicators and/or dispensers are provided whereby an amount of adhesive or sealant material may be conveniently applied. The applicators and/or dispensers can be either disposable or reusable, depending on the desired application.

In embodiments, an applicator and/or dispenser is designed to facilitate manipulation by hand for mixing, dispensing and/or applying an adhesive or sealant. For example, in embodiments of this invention, applicators and/or dispensers are provided that are pen-like, providing a familiar feel to the user. In embodiments, an applicator and/or dispenser is designed to be more comfortable to the user, easier to grip and/or easier to operate.

In embodiments, an applicator and/or dispenser includes a polymerization rate modifier, such as, for example, an initiator or accelerator, for the adhesive or sealant material. The polymerization rate modifier may be disposed in or on a part of the applicator. The polymerization rate modifier may be absorbed or adsorbed into a porous portion of the applicator, may be coated on a surface of the applicator, or otherwise incorporated into a portion of the applicator. The applicator and/or dispenser may also include a frangible barrier separating first and second compartments, for example, to keep the polymerization rate modifier or other component separated from the adhesive or sealant material or other component prior to use.

In particular, this invention is directed to an applicator/dispenser for dispensing, mixing and/or applying an adhesive or sealant material, comprising: a body portion; an actuator movable relative to the body portion; a cavity in the body portion; and a piercing or breaking portion on the actuator, wherein movement of the actuator relative to the body portion moves the piercing or breaking portion into the cavity. In various embodiments, the applicator/dispenser further comprises a container of adhesive or sealant material at least partially disposed within the cavity, wherein movement of the actuator relative to the body portion moves the piercing or breaking portion to rupture the container.

In embodiments, the adhesive or sealant material comprises a polymerizable monomeric adhesive or sealant material. In embodiments, the adhesive or sealant material comprises a polymerizable 1,1-disubstituted ethylene monomer formulation. In still other embodiments, the adhesive or sealant material comprises a cyanoacrylate formulation.

In embodiments, the applicator/dispenser includes a polymerization initiator or accelerator for the adhesive or sealant material.

In embodiments, the applicator/dispenser further comprises a pivoting connection that movably connects the actuator and the body portion. In embodiments, the body portion comprises a handle portion of the applicator/dispenser. In embodiments, movement of the actuator relative to the body portion to move the piercing or breaking portion into the cavity is inhibited prior to use of the applicator/dispenser. In embodiments, the actuator comprises a lever movably mounted on the body portion.

In embodiments, the applicator/dispenser further comprises: a bladder disposed at least partially within the cavity, at least a portion of the bladder being flexible; and a container of adhesive or sealant material disposed within the bladder and at least partially located in the cavity, wherein movement of the actuator relative to the body portion moves the piercing or breaking portion to rupture the container.

In embodiments, the applicator/dispenser further comprises a second container having at least one opening, the second container at least partially surrounding the container of adhesive or sealant, wherein movement of the actuator relative to the body portion moves the piercing or breaking portion to rupture the container containing the adhesive or sealant without breaking the second container.

In embodiments, the applicator/dispenser further comprises a plug member at least partially disposed in an opening of the bladder or the second container, the plug member being made of a material that is at least one of porous, absorbent and adsorbent in nature. In embodiments, at least one of a medicament, a polymerization initiator, a polymerization rate modifier and a stabilizer for a polymerizable monomer is in or on the plug member.

In embodiments, the applicator/dispenser further comprises an applicator/dispenser tip that is connected to the body portion. In embodiments, the applicator/dispenser tip comprises one of a tube, a nozzle, a spatula, a rolling ball, a brush, and a swab. In embodiments, the applicator/dispenser tip is removable. In embodiments, the applicator/dispenser further comprises a machined orifice disposed between the cavity and the applicator/dispenser tip, the machined orifice providing a restricted flow of a material when the material is being dispensed from the applicator/dispenser.

In embodiments, the applicator/dispenser further comprises: a mixing chamber that communicates with the cavity; and a dispensing opening that communicates with at least one of the cavity and the mixing chamber.

In embodiments, the applicator/dispenser further comprises a valve that selectively establishes communication between at least two of: the cavity and the mixing chamber; the cavity and the dispensing opening; and the cavity, the mixing chamber and the dispensing opening. In embodiments, the valve comprises: a first portion; and a second portion movable relative to the first portion to selectively establish communication between at least two of: the cavity and the mixing chamber; the cavity and the dispensing opening; and the cavity, the mixing chamber and the dispensing opening. In embodiments, the first portion comprises a valve stem, the second portion comprises a valve sleeve rotatably mounted over a portion of the valve stem, and rotation of the valve sleeve relative to the valve stem establishes different flow paths through the valve. In embodiments, the second portion inhibits movement of the actuator when the second portion is in a predetermined position.

In embodiments, the applicator/dispenser further comprises an applicator/dispenser tip that is attached to at least one of the valve and the body portion. In embodiments, the applicator/dispenser tip comprises one of a tube, a nozzle, a spatula, a rolling ball, a brush, and a swab. In embodiments, the applicator/dispenser tip is removable. In embodiments, the applicator/dispenser further comprises a machined orifice disposed between the valve and the applicator/dispenser tip, the machined orifice providing a restricted flow of a material when the material is being dispensed from the applicator/dispenser.

In other embodiments, this invention is directed to a kit comprising: at least one applicator/dispenser; and a plurality of containers of adhesive or sealant material arranged to be placed at least partially in the cavity of the at least one applicator/dispenser, wherein movement of the actuator relative to the body portion moves the piercing or breaking portion to rupture one of the containers that is placed at least partially in the cavity. In embodiments, the kit further comprises a plurality of removable applicator tips. In embodiments, the kit further comprises a polymerization initiator or rate modifier for the adhesive or sealant material. In embodiments, at least two of the plurality of containers contain different amounts of adhesive or sealant material. In other embodiments, at least two of the plurality of containers contain a different adhesive or sealant material.

In other embodiments, this invention is directed to a method of applying/dispensing an adhesive or sealant material comprising: placing a container of adhesive or sealant material at least partially into the cavity of an applicator/dispenser;

moving the actuator relative to the body portion to move the piercing or breaking portion to rupture the container; and dispensing the adhesive or sealant material from the applicator/dispenser. In embodiments, the method further comprises applying the dispensed adhesive or sealant to a substrate to be bonded. In embodiments, the method further comprises mixing the adhesive or sealant material with a second material prior to dispensing the adhesive or sealant material from the applicator/dispenser. In embodiments, the second material comprises at least one of a medicament, a polymerization initiator, a polymerization rate modifier and a stabilizer for a polymerizable monomer.

In other embodiments, this invention allows for a "hands forward" position on the applicator/dispenser providing greater control over placement of the adhesive or sealant material. Additionally, the placement and length of the actuator allows for ease of use of the applicator while maintaining the hands forward position thereby allowing for greater control over the flow and direction of the adhesive or sealant.

Various other features and advantages of this invention will be apparent from the following detailed description of exemplary embodiments.

BRIEF DESCRIPTION OF THE DRAWINGS

Exemplary embodiments of this invention are described in detail below, with reference to the attached drawing figures, in which:

FIG. 10 is an enlarged perspective view of the valve stem of the exemplary embodiment of FIG. 7;

FIGS. 11-13 are enlarged cross-sectional views of the valve stem of FIG. 10;

DETAILED DESCRIPTION OF EXEMPLARY EMBODIMENTS

In embodiments of this invention, an applicator/dispenser is provided that facilitates easy application of a desired quantity of polymerizable adhesive or sealant material. In embodiments, an amount of polymerizable adhesive or sealant material is prepackaged in the applicator/dispenser in a frangible ampoule that is broken upon activation of the applicator/dispenser. The frangible ampoule may provide stability and/or shelf-life for the amount of polymerizable adhesive or sealant material.

Figure 1:
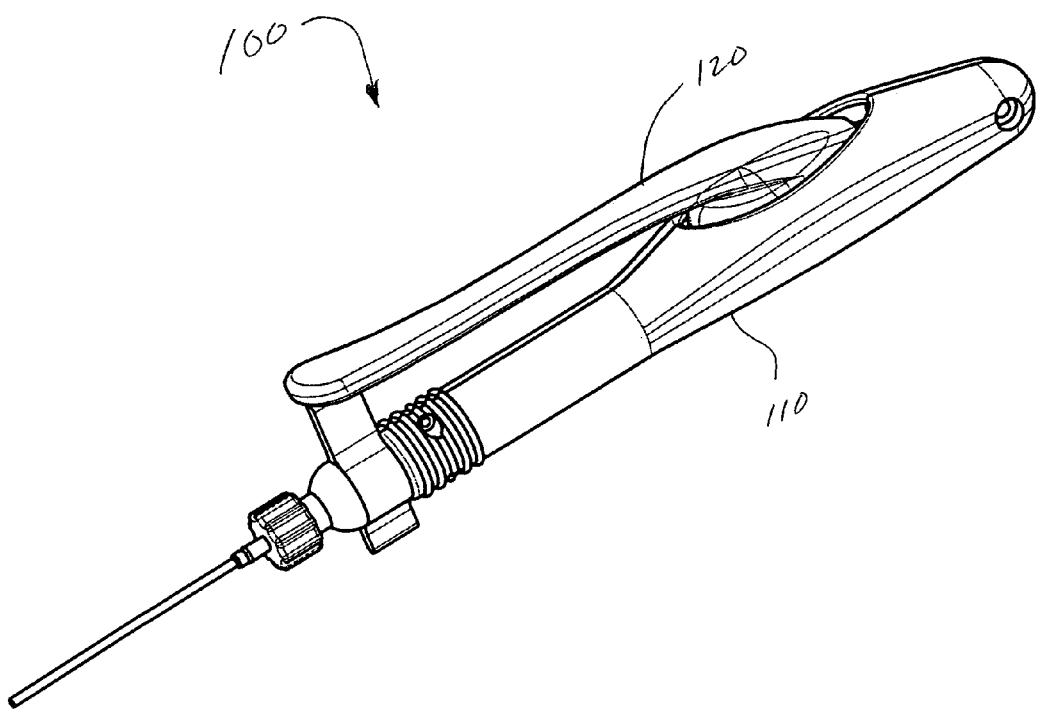
FIG. 1 is a perspective view of a first exemplary embodiment of this invention.
Figure 2:
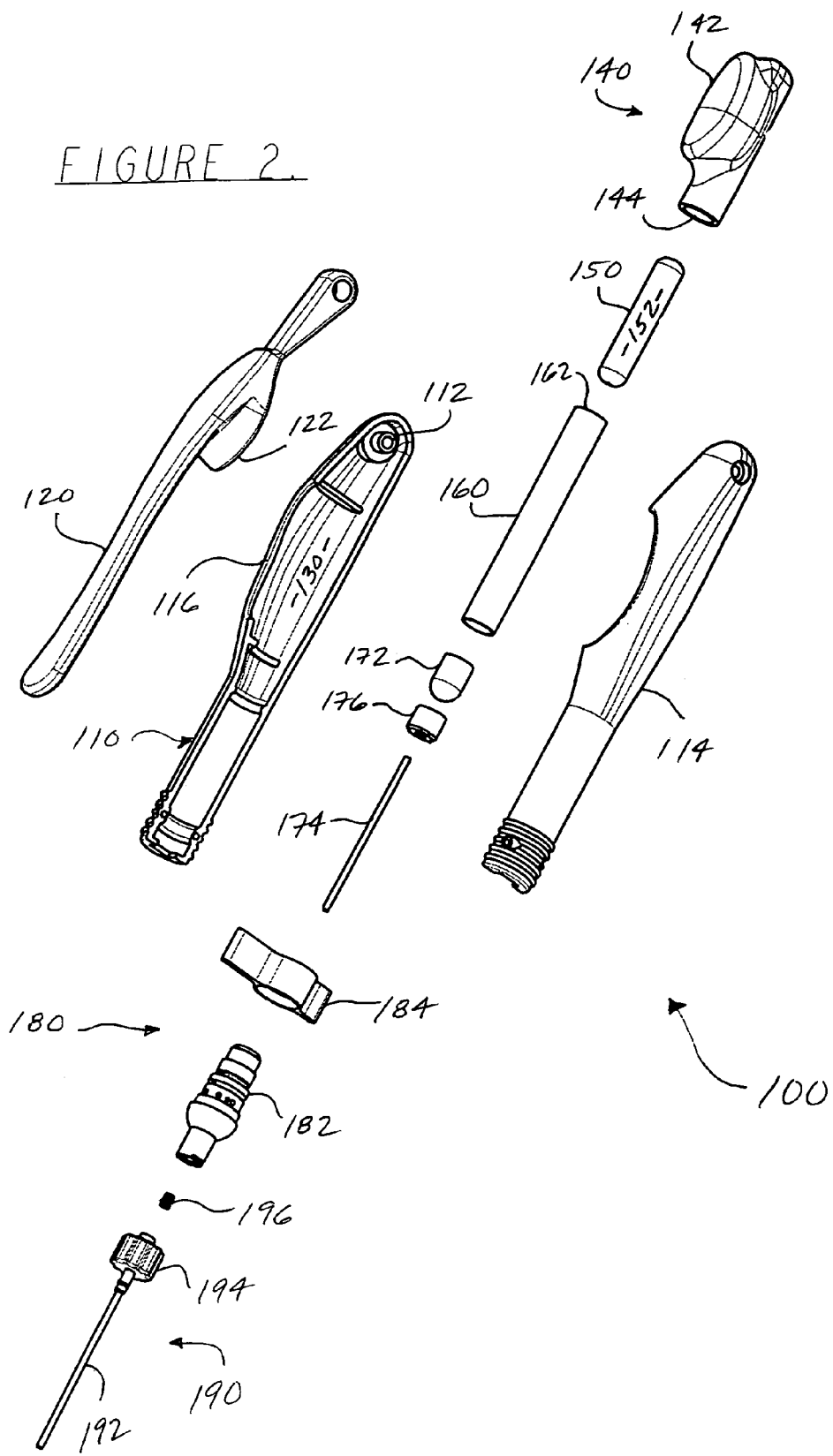
FIG. 2 is an exploded perspective view of the exemplary embodiment of FIG. 1.
Figure 3:
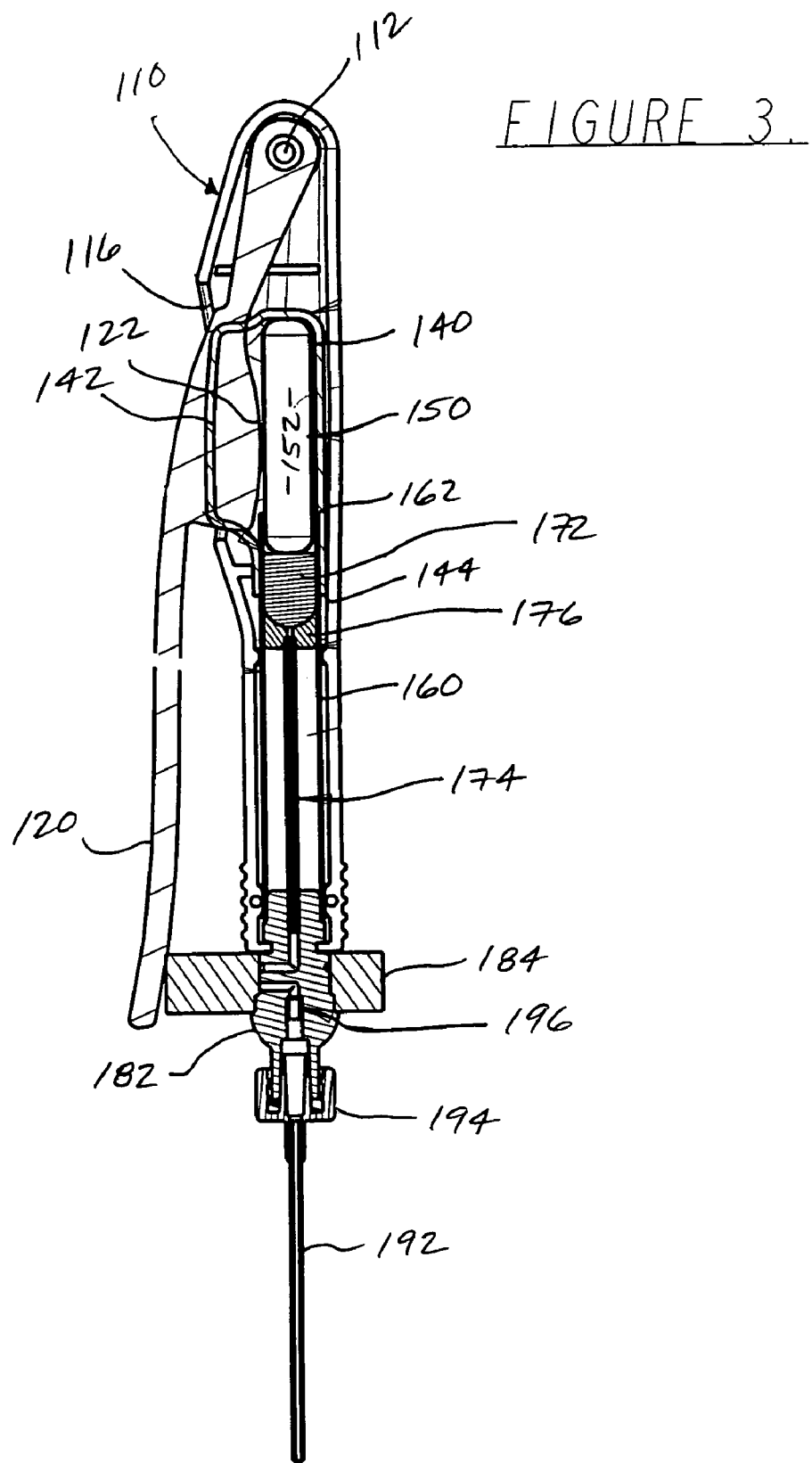
FIG. 3 is a cross-sectional view of the exemplary embodiment of FIG. 1 with the valve in a first position.

FIGS. 1-6 illustrate a first embodiment of this invention, although this invention is in no way limited to the specific design depicted therein. As shown in FIGS. 1-3, an applicator/dispenser 100 is formed by a body portion 110 and an actuator 120 that is movable relative to the body portion 110. For example, in the embodiment shown, a pivoting connection 112 is provided that allows the actuator 120 to be moved relative to the body portion 110.

As shown in FIG. 2, the body portion 110 may comprise a first body portion 114 and a second body portion 116 that are fitted together in a suitable manner. The pivoting connection 112 may be defined by respective portions of the first and second body portions 114, 116. Further, a cavity 130 may be disposed in the body portion 110 and may be defined thereby.

A piercing or breaking portion 122 may be defined on the actuator 120. Movement of the actuator 120 relative to the body portion 110 moves the piercing or breaking portion 122 into the cavity 130.

A bladder 140 may be fitted in the cavity 130. As shown in FIGS. 1 and 2, the body portion 110 has an opening through which the actuator 120 extends. The bladder 140 may be positioned, for example, in the vicinity of the opening such that a push button portion 142 of the bladder 140 is contacted by the actuator 120 when the actuator 120 is depressed toward the body portion 110. As explained below, the push button portion 142 may thus be depressed by a user to dispense a desired quantity of polymerizable adhesive or sealant material from the applicator/dispenser 100, for example, through a fixed, detachable or replaceable tip 190. A user may apply pressure on the push button portion 142 by depressing the actuator 120 while the applicator/dispenser 100 is held by the body portion 110 as a handle. For example, a user may hold the applicator/dispenser 100 as a pen and press the actuator 120 with an index finger. As further described below, the actuator 120 may also be depressed by a user to mix a polymerizable adhesive or sealant material with a second material prior to dispensing.

It should be understood that the fixed, detachable or replaceable tip 190 may have any desired configuration. As shown, the tip 190 comprises a tube 192 that may be attached or connected to the body portion 110, for example, by a connector 194, such as a conventional luer connector. The tip 190 may be selected for a particular application such as vascular surgery, and is not limited to the tube 192 shown. For example, the applicator tip may be a fibrous swab, a sponge swab, a foam swab, a brush, a spatula or the like. Any suitable tip, either known or hereafter developed, may be used with the applicators/dispensers according to this invention.

The tip 190 may be designed to friction fit over or within an end portion of the body portion 110, for example, via screw threads. Alternatively, the tip 190 may fit directly on a valve 180 that is situated in an open end of the body portion 110, as described below.

A frangible ampoule 150 containing an amount of polymerizable adhesive or sealant 152 is disposed in the bladder 140. The frangible ampoule 150 may be made of any suitable material, preferably a material that promotes stability and shelf-life of the polymerizable adhesive or sealant material 152. For example, the frangible ampoule 150 may be made of glass. Other materials, such as, a plastic material or pierceable metal, such as aluminum, may be used for the frangible ampoule 150. An example of a suitable ampoule that can be used in the dispenser/applicators of the present invention is disclosed in, for example, U.S. Pat. No. 5,928,611, the entire disclosure of which is incorporated herein by reference. In fact, where such an ampoule is used in the present invention, the entire ampoule/applicator device may be used, which would thereby constitute not only the ampoule 150, but also a porous plug 172. In such embodiments, the dispensers/applicators of the present invention are particularly suitable for dispensing or applying the adhesive or sealant contained in the DERMABOND® topical skin adhesive or sealant product, available from Ethicon (Somerville, N.J.).

The bladder 140 has an open end 144 into which the second container 160 is fitted. At least the push button portion 142 of the bladder 140 is made of a flexible material. The bladder 140 is made of a suitable rubber, silicone or plastic material, such as, for example, polyvinyl chloride, polyethylene, polyurethane, natural or nitril rubber, or any combination thereof.

The porous plug 172 may include a polymerization initiator or rate modifier for the polymerizable adhesive or sealant material to be dispensed. The porous plug 172 may be impregnated with the polymerization initiator or rate modifier, or may have the polymerization initiator or rate modifier coated on a surface thereof.

In the first embodiment, the ampoule 150 is surrounded by a second container 160, such as a butyrate tube as shown. The second container 160 may be of any suitable material that is compatible with the particular adhesive or sealant to be applied, such as, for example, butyrate or polyethylene, and may be selected based on a desired application. Movement of the actuator 120 relative to the body portion 110 preferably moves the piercing or breaking portion 122 to rupture the ampoule 150 without breaking the second container 160.

As shown, the second container 160 has at least one hole 162 formed therein. When assembled, the second container 160 is positioned in the bladder 140 so that the hole 162 is placed in communication with the interior of the push button portion 142 of the bladder 140, at least once the ampoule 150 is broken. As described below, this allows the depression of the push button portion 142 to apply pressure to expel the adhesive or sealant 152. In embodiments, the second container 160 is fixed or bonded to the bladder 140 so that the hole 162 is maintained in a proper position.

The bladder 140, the push button portion 142, the frangible ampoule 150, the second container 160 and the porous plug 172 may be assembled and inserted into the cavity 130 of the body portion 110, as shown in FIG. 3. The second container 160 may define a mixing chamber in which a siphon tube 174 is disposed. The siphon tube 174 may be mounted on a plug cap 176 that is fitted over the porous plug 172 and provides communication between the porous plug 172 and the siphon tube 174.

The applicator/dispenser 100 further includes the valve 180 that selectively establishes communication between at least two of: the bladder 140 disposed in the cavity 130, and the mixing chamber of the second container 160; the bladder 140 and a dispensing opening that leads to the applicator tip 190; and the bladder 140, the mixing chamber of the second container 160 and the dispensing opening that leads to the applicator tip 190. In the embodiment shown, the valve 180 comprises a first portion 182 and a second portion 184 movable relative to the first portion 182 to selectively establish communication. The first portion 182 may comprise a valve stem and the second portion 184 may comprise a valve sleeve that is rotatably mounted over a portion of the valve stem.

Figure 5:
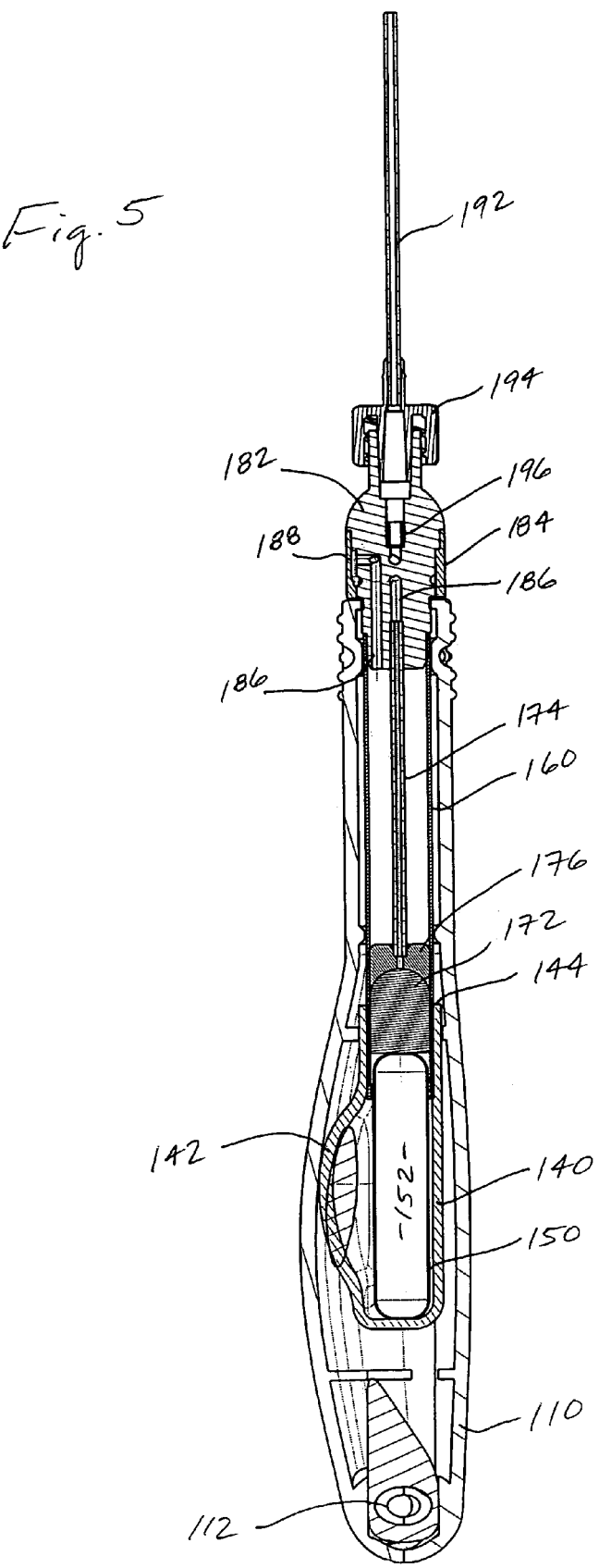
FIG. 5 is a cross-sectional view of the exemplary embodiment of FIG. 1 with the valve in a second position.
Figure 6:
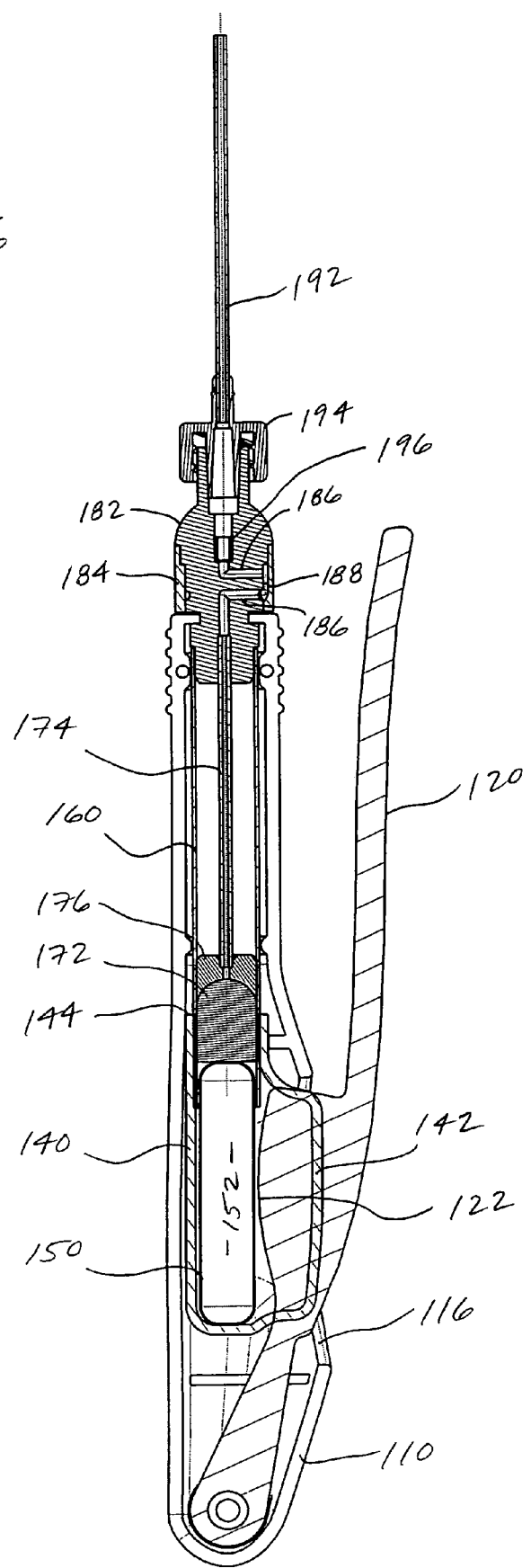
FIG. 6 is a cross-sectional view of the exemplary embodiment of FIG. 1 with the valve in a third position.

The valve sleeve 184 may be rotated relative to the valve stem 182 to establish different flow paths through the valve 180. The different flow paths may be defined, for example, by a plurality of bores 186 formed in the valve stem 182. As the valve sleeve 184 is rotated relative to the valve stem 182, a cutout or groove 188 on an inner surface of the valve sleeve 184 establishes different flow paths by selectively communicating with the plurality of bores 186. The different flow paths establishing communication between the bladder 140, the mixing chamber of the second container 160 and/or the dispensing opening that leads to the applicator tip 190 are illustrated in FIGS. 4-6.

In the first embodiment, a machined orifice 196 may be disposed in the dispensing opening that leads to the applicator tip 190, for example, in an end of the valve stem 182. The machined orifice 196 is disposed between the bladder 140, and the tip 190 to provide a restricted flow of a material when the material is being dispensed from the applicator/dispenser 100.

As illustrated in FIG. 3, the valve sleeve 184 may be positioned to inhibit movement of the actuator 120 prior to use of the applicator/dispenser 100. This may help avoid premature breakage of the ampoule 150 and, for example, premature polymerization of the adhesive or sealant material 152.

Figure 4:
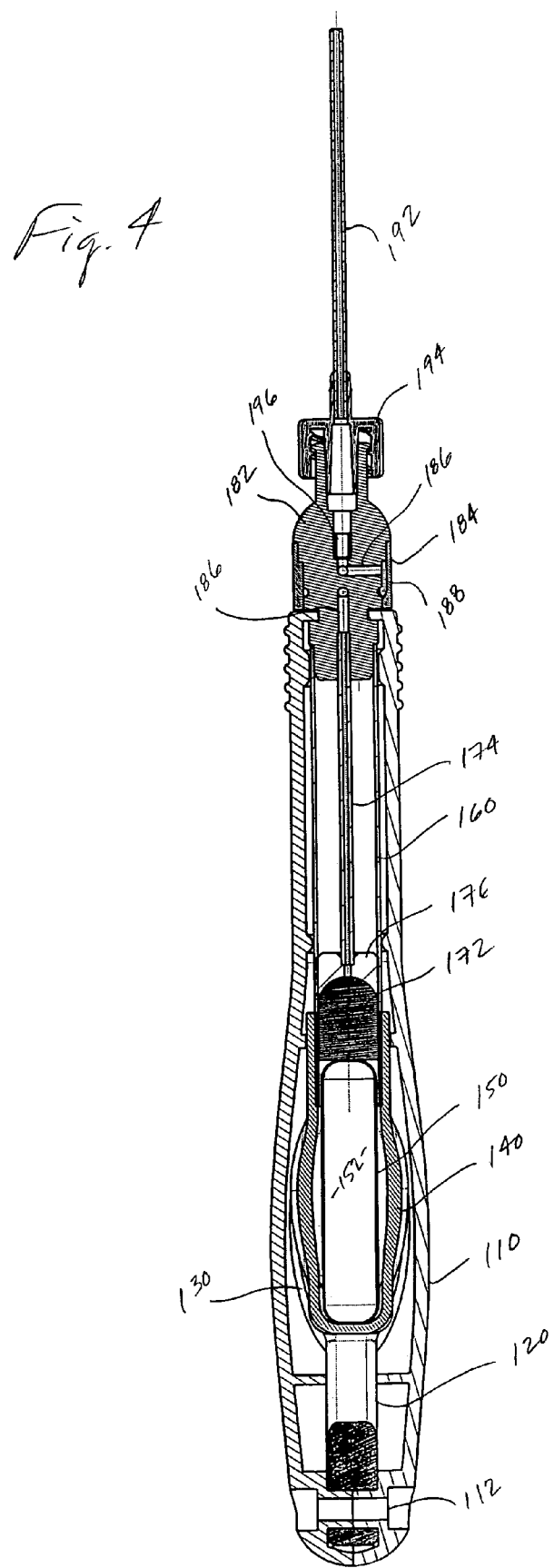
FIG. 4 is a different cross-sectional view of the exemplary embodiment of FIG. 1 with the valve in the first position.

As illustrated in FIG. 4, the valve sleeve 184 may be positioned in a first position in which the cutout or groove 188 of the valve sleeve 184 establishes a flow path by communicating with one of the plurality of bores 186 such that communication is established between the cavity 130, the mixing chamber of the second container 160 and the dispensing opening that leads to the applicator tip 190. The first position of the valve sleeve 184 may be used to allow for EtO sterilization, for example. The first position of the valve sleeve 184 may also be position that inhibits movement of the actuator 120 prior to use of the applicator/dispenser 100.

As illustrated in FIG. 5, the valve sleeve 184 may be positioned in a second position, for example, by rotating the valve sleeve 184 relative to the valve stem 182. In the second position, the cutout or groove 188 of the valve sleeve 184 establishes a flow path by communicating with a different one of the plurality of bores 186 such that communication is established between the bladder 140 and the mixing chamber of the second container 160. The second position of the valve sleeve 184 may be used to allow for mixing of the adhesive or sealant material 152 with another material, as further described below.

As illustrated in FIG. 6, the valve sleeve 184 may be positioned in a third position, for example, by rotating the valve sleeve 184 relative to the valve stem 182. In the third position, the cutout or groove 188 of the valve sleeve 184 establishes a flow path by communicating with yet a different one of the plurality of bores 186 such that communication is established between the bladder 140 and the dispensing opening that leads to the applicator tip 190. The third position of the valve sleeve 184 may be used to allow the adhesive or sealant material 152 to be dispensed, as further described below.

In use, the valve sleeve 184 is moved from its initial position shown in FIG. 3, for example, by rotating the valve sleeve 184 relative to the valve stem 182, to allow the actuator 120 to be moved relative to the body portion 110. The actuator 120 is then moved relative to the body portion 110 so that the piercing or breaking portion 122 is moved into the cavity 130 and breaks the ampoule 150 to release the adhesive or sealant material 152 into the bladder 140.

When mixing of the adhesive or sealant material 152 is desired, for example, with a second material such as an initiator or polymerization rate modifier, the valve sleeve 184 is then moved to the second position shown in FIG. 5. The adhesive or sealant material 152 may be forced from the bladder 140, through the porous plug 172 and into the mixing chamber of the second container 160 via the siphon tube 174 by depressing the actuator 120 against the push button portion 142 of the bladder 140, to apply pressure, displace the adhesive or sealant material 152 and cause the adhesive or sealant material 152 to flow through the porous plug 172. The adhesive or sealant material 152 and the second material, contained in the porous plug, for example, are mixed in the mixing chamber of the second container 160 and drawn back into the bladder 140 by the siphon tube 174 by depressing the actuator 120, for example, multiple times.

When dispensing of the adhesive or sealant material 152 is desired, the valve sleeve 184 is then moved to the third position shown in FIG. 6. A controlled flow of the adhesive or sealant material 152 may be obtained by depressing the actuator 120 against the push button portion 142 to a desired extent and/or a desired number of times with the valve sleeve 184 in the third position. The machined orifice 196 may be used to restrict the flow of the adhesive or sealant material 152, for example, so that a steady flow may be established and/or so that an undesired spurt of the adhesive or sealant material 152 does not occur. In embodiments, the volume displaced by depressing the push button portion 142 (via the actuator 120) may correspond to a desired metered amount of the adhesive or sealant material 152 that is to be dispensed.

The amount of adhesive or sealant material 152 may be prepackaged in the applicator/dispenser 100. The applicator/dispenser 100 may be disposable and discarded after the amount of adhesive or sealant material 152 in the frangible ampoule 150 has been dispensed or otherwise been used (i.e., polymerized). Alternatively, the amount of adhesive or sealant material 152 may be separate from the applicator/dispenser 100 and supplied to the applicator/dispenser 100 prior to use.

In embodiments, a user may be able to select from a variety of adhesive or sealant materials and/or amounts by selecting a frangible ampoule and/or bladder assembly (bladder, ampoule and plug) to be installed in the applicator/dispenser 100.

For example, a kit may be provided that includes at least one applicator/dispenser 100 and a plurality of frangible ampoules 150 (or bladder assemblies). A plurality of detachable or replaceable tips 190 may also be included in the kit. The kit may also include a cleaning agent, such as isopropyl alcohol or other chemical sterilants, such as gluteraldehyde. Parts of the kit, such as the frangible ampoules 150 (or bladder assemblies) may be packaged separately, for example, in a blister pouch, and may be unpackaged and combined with the applicator/dispenser 100 as needed.

Figure 7:
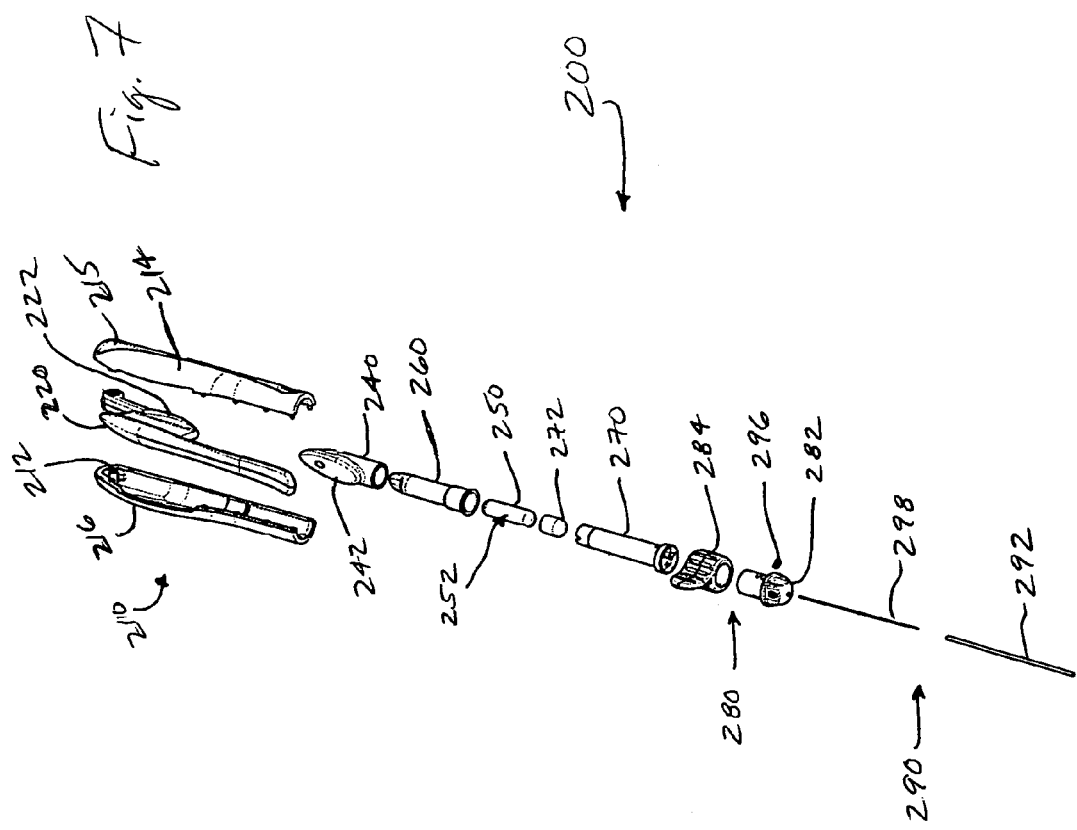
FIG. 7 is an exploded perspective view of a second exemplary embodiment of this invention.

FIGS. 7-19 illustrate a second embodiment of this invention, although this invention is in no way limited to the specific design depicted therein. As shown in FIG. 7, an applicator/dispenser 200 is formed by a body portion 210 and an actuator 220 that is movable relative to the body portion 210. For example, in the embodiment shown, a pivoting connection 212 is provided that allows the actuator 220 to be moved relative to the body portion 210.

As shown in FIG. 7, the body portion 210 may comprise a first body portion 214 and a second body portion 216 that are fitted together in a suitable manner. An outer portion 215 of the first and second body portions 214, 216 may be made of a softer material for comfort and/or grip of a user. The pivoting connection 212 may be defined by respective portions of the first and second body portions 214, 216. Further, a cavity may be defined in the body portion 210, for example, upon assembly of the first and second body portions 214, 216.

A piercing or breaking portion 222 may be defined on the actuator 220. Movement of the actuator 220 relative to the body portion 210 moves the piercing or breaking portion 222 into the cavity.

A bladder 240 may be fitted in the cavity. As shown in FIG. 7, the body portion 210 defines an opening through which the actuator 220 extends when the first and second body portions 214 and 216 are fitted together. The bladder 240 may be positioned, for example, in the vicinity of the opening such that a push button portion 242 of the bladder 240 is contacted by the actuator 220 when the actuator 220 is depressed toward the body portion 210. As explained below, the push button portion 242 may thus be depressed by a user to dispense a desired quantity of polymerizable adhesive or sealant material from the applicator/dispenser 200, for example, through a fixed, detachable or replaceable tip 290. A user may apply pressure on the push button portion 242 by depressing the actuator 220 while the applicator/dispenser 200 is held by the body portion 210 as a handle. For example, a user may hold the applicator/dispenser 200 as a pen and press the actuator 220 with an index finger. As further described below, the actuator 220 may also be depressed by a user to mix a polymerizable adhesive or sealant material with a second material prior to dispensing.

It should be understood that the fixed, detachable or replaceable tip 290 may have any desired configuration. As shown, the tip 290 comprises a tube 292 that may be attached or connected directly to a valve stem 282, described further below. The tip 290 may be designed to friction fit in a bore of the valve stem 282. The tip 290 may be selected for a particular application such as vascular surgery, and is not limited to the tube 292 shown. For example, the applicator tip may be a fibrous swab, a sponge swab, a foam swab, a brush, a spatula or the like. Any suitable tip, either known or hereafter developed, may be used with the applicators/dispensers according to this invention.

A frangible ampoule 250 containing an amount of adhesive or sealant material 252 is disposed in the bladder 240. As discussed above, the frangible ampoule 250 may be made of any suitable material, preferably a material that promotes stability and shelf-life of the adhesive or sealant material 252. At least the push button portion 242 of the bladder 240 is made of a flexible material. The bladder 240 may be blow molded of a suitable rubber, silicone or plastic material, such as, for example, polyvinyl chloride, polyethylene, polyurethane, natural or nitril rubber, or any combination thereof.

Figure 8:
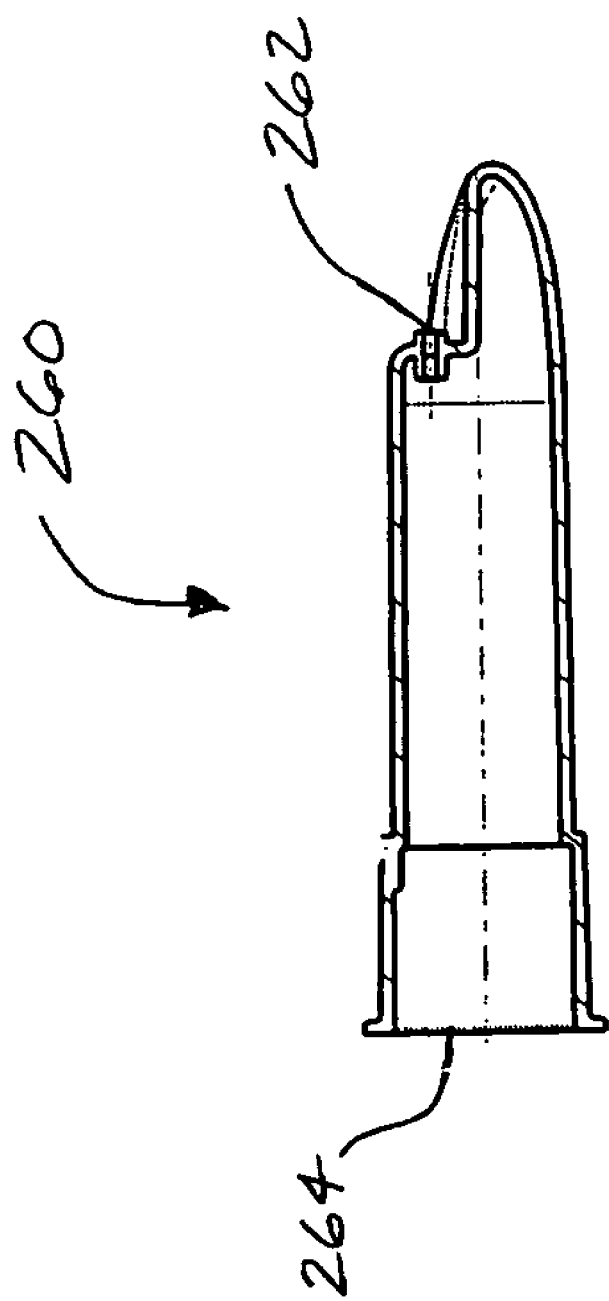
FIG. 8 is an enlarged cross-sectional view of the ampoule chamber of the exemplary embodiment of FIG. 7.

In the second embodiment, the ampoule 250 is surrounded by a second container 260, such as a tube, as shown in detail in FIG. 8. The second container 260 may be of any suitable material that is compatible with the particular adhesive or sealant to be applied, such as, for example, butyrate or polyethylene, and may be selected based on a desired application. Movement of the actuator 220 relative to the body portion 210 preferably moves the piercing or breaking portion 222 to rupture the ampoule 250 without breaking the second container 260.

As shown, the second container 260 has at least one hole 262 formed therein. When assembled, the second container 260 is positioned in the bladder 240 so that the hole 262 is placed in communication with the interior of the push button portion 242 of the bladder 240. As described below, this allows the depression of the push button portion 242 to apply pressure to expel the adhesive or sealant 252. In embodiments, the second container 260 is fixed or bonded to the bladder 240 so that the hole 262 is maintained in a proper position.

The second container 260 also has an open end 264 into which a porous plug 272 may be fitted, as illustrated in FIG. 7. The porous plug 272 may include a polymerization initiator or rate modifier for the polymerizable adhesive or sealant material to be dispensed. The porous plug 272 may be impregnated with the polymerization initiator or rate modifier, or may have the polymerization initiator or rate modifier coated on a surface thereof.

The bladder 240, the push button portion 242, the frangible ampoule 250, the second container 260 and the porous plug 272 may be assembled and inserted into the cavity of the body portion 210. Further, a second tube 270 may be disposed in the body portion 210 adjacent the porous plug 272.

Figure 9:
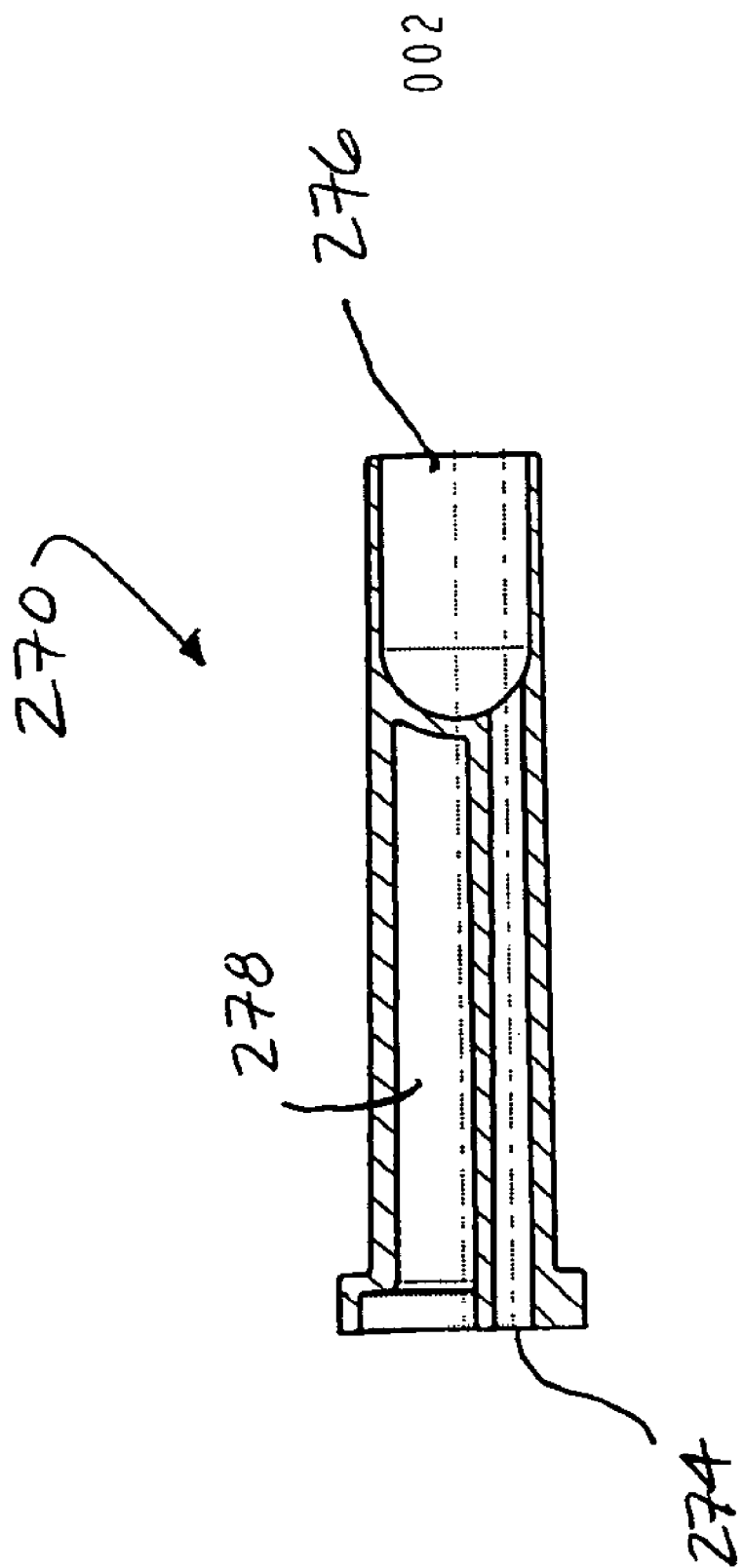
FIG. 9 is an enlarged cross-sectional view of the mixing chamber of the exemplary embodiment of FIG. 7.

For example, as shown in FIG. 9, the second tube 270 may include a plug portion 276 that is configured to receive the porous plug 272. The second tube 270 may define a mixing chamber 278 which may be communicated with the plug portion 276 via a siphon bore 274 defined by the second tube 270.

The applicator/dispenser 200 further includes a valve 280 that selectively establishes communication between at least two of: the bladder 240 disposed in the cavity, and the mixing chamber 278; the bladder 240 and a dispensing opening that leads to the applicator tip 290; and the bladder 240, the mixing chamber 278 and the dispensing opening that leads to the applicator tip 290. In the embodiment shown, the valve 280 comprises a first portion 282 and a second portion 284 movable relative to the first portion 282 to selectively establish communication. The first portion 282 may comprise a valve stem and the second portion 284 may comprise a valve sleeve that is rotatably mounted over a portion of the valve stem.

Figure 14:
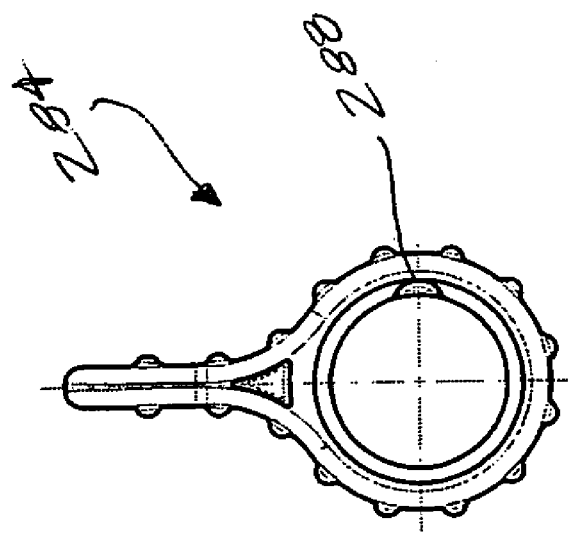
FIG. 14 is an enlarged axial view of the valve of the exemplary embodiment of FIG. 7.
Figure 15:
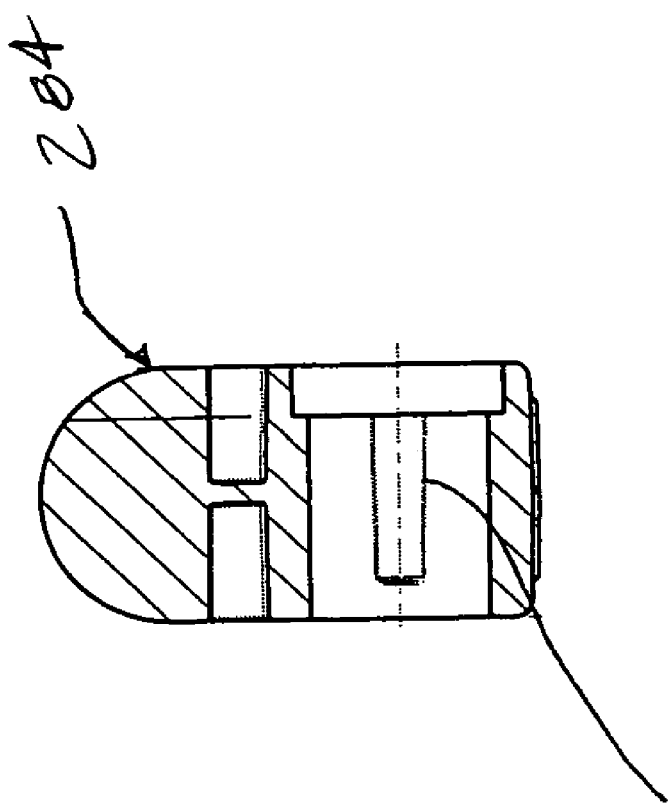
FIG. 15 is a cross-sectional view of the valve of FIG. 7.

The valve sleeve 284 may be rotated relative to the valve stem 282 to establish different flow paths through the valve 280. The different flow paths may be defined, for example, by a plurality of channels 286 formed in the valve stem 282. Details of the valve stem 282 are shown in FIGS. 10-13. As the valve sleeve 284 is rotated relative to the valve stem 282, a cutout or groove 288 on an inner surface of the valve sleeve 284 establishes different flow paths by selectively communicating with the plurality of channels 286, acting as a three-way valve. Details of the valve sleeve 284 are shown in FIGS. 14-15.

Figure 16:
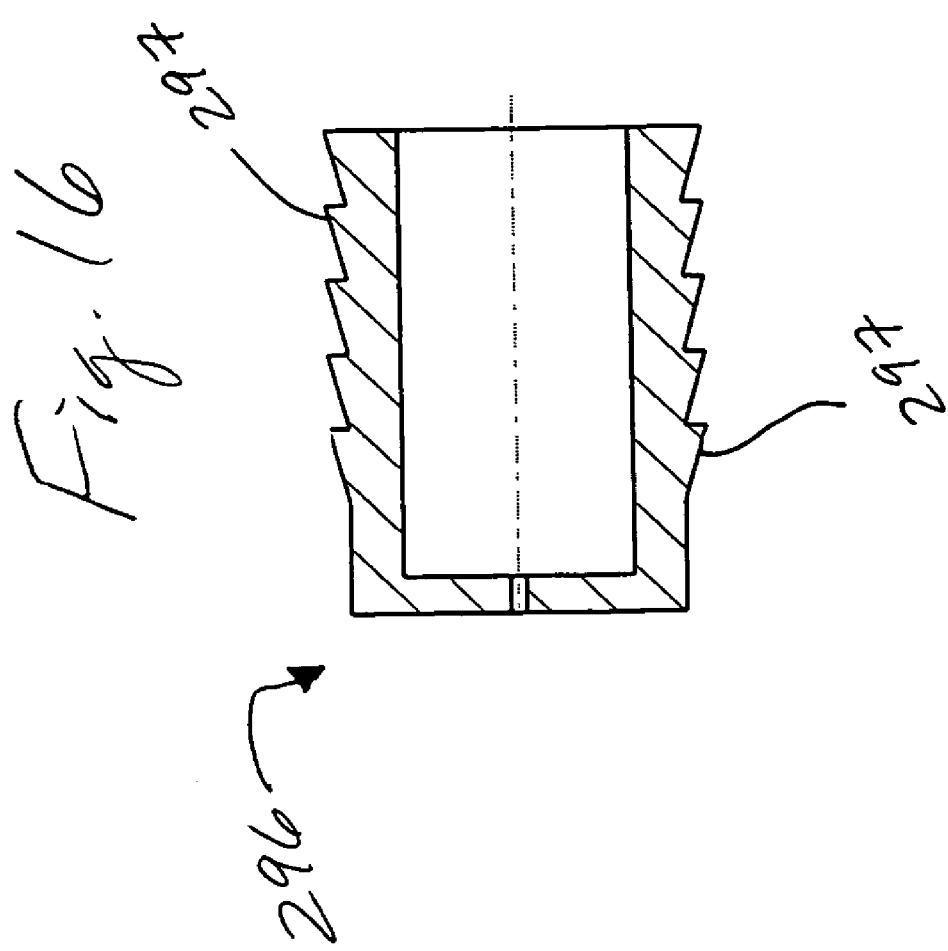
FIG. 16 is an enlarged cross-sectional view of the orifice of the exemplary embodiment of FIG. 7.

In the second embodiment, a machined orifice 296 may be disposed in the valve stem 282, for example, in an end of the valve stem 282 adjacent to the mixing chamber 278. The machined orifice 296 is disposed between the cavity 230, i.e., the bladder 240, and the tip 290 to provide a restricted flow of a material when the material is being dispensed from the applicator/dispenser 200. The machined orifice 296 may thus add to the user's control over flow of the adhesive or sealant material as it is dispensed. Details of the machined orifice 296 are shown in FIG. 16. For example, the machined orifice 296 may optionally have a plurality of annular ridges 297 to secure the machined orifice 296 in the valve stem 282. The machined orifice 296 may have a precision hole, for example, of about 0.0045 inches.

Figure 17:
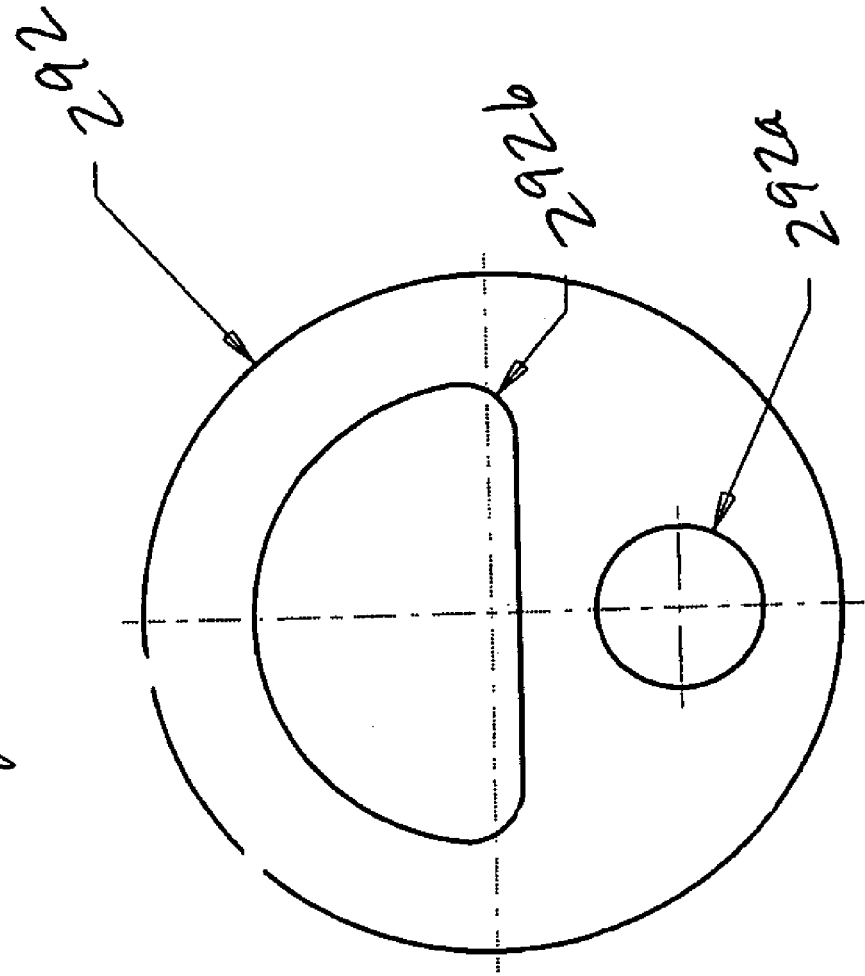
FIG. 17 is an enlarged axial view of the dispensing tube of the exemplary embodiment of FIG. 7.

As shown in FIG. 7, the applicator/dispenser 200 may include a malleable wire 298. The malleable wire 298 may be disposed in the applicator tip 292, for example, in an auxiliary portion 292a that runs parallel to a main portion 292b through which the adhesive or sealant may flow, as shown in FIG. 17. The applicator tip 292 may comprise a flexible tube such that the applicator tip 292 and the malleable wire 298 may be bent to a desired shape, with the malleable wire 298 maintaining the applicator tip 292 substantially in the desired shape, for example, for facilitating application. The separate portions 292a and 292b may also enhance the user's ability to visualize flow of the adhesive or sealant material as it is dispensed.

Figure 18:
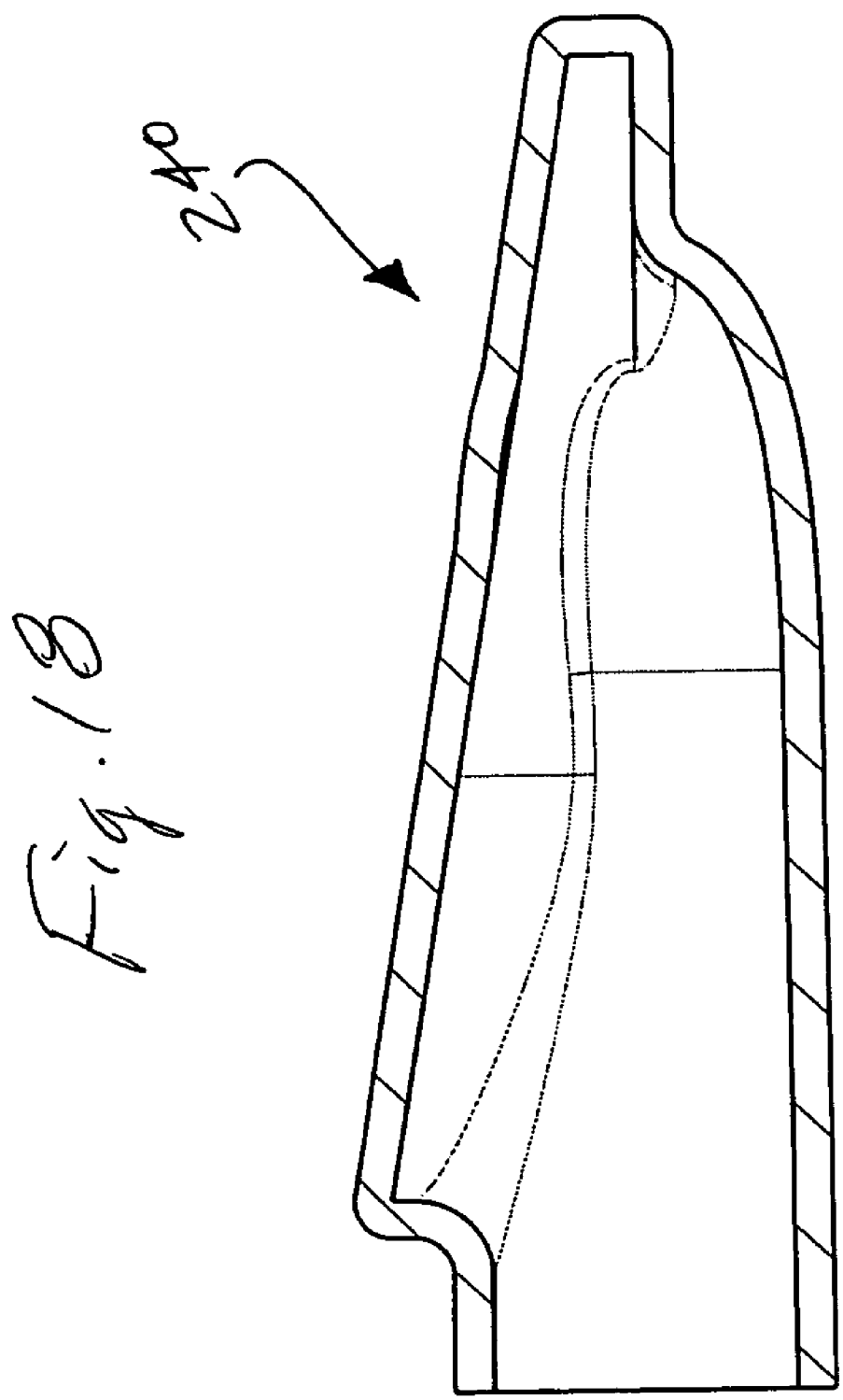
FIG. 18 is a cross-sectional view of the bladder of the exemplary embodiment of FIG. 7.

Details of the bladder 240 are shown in FIG. 18. The bladder 240 should be large enough to facilitate dispensing of all of the adhesive or sealant material through compression of the bladder 240. Further, the bladder 240 should be resilient enough to substantially return to its initial shape once the actuator 220 is released. The bladder 240 should be airtight and should be attached to the tube 260 in an airtight manner so that compression of the bladder forces the adhesive or sealant material through the applicator 200.

Figure 19:
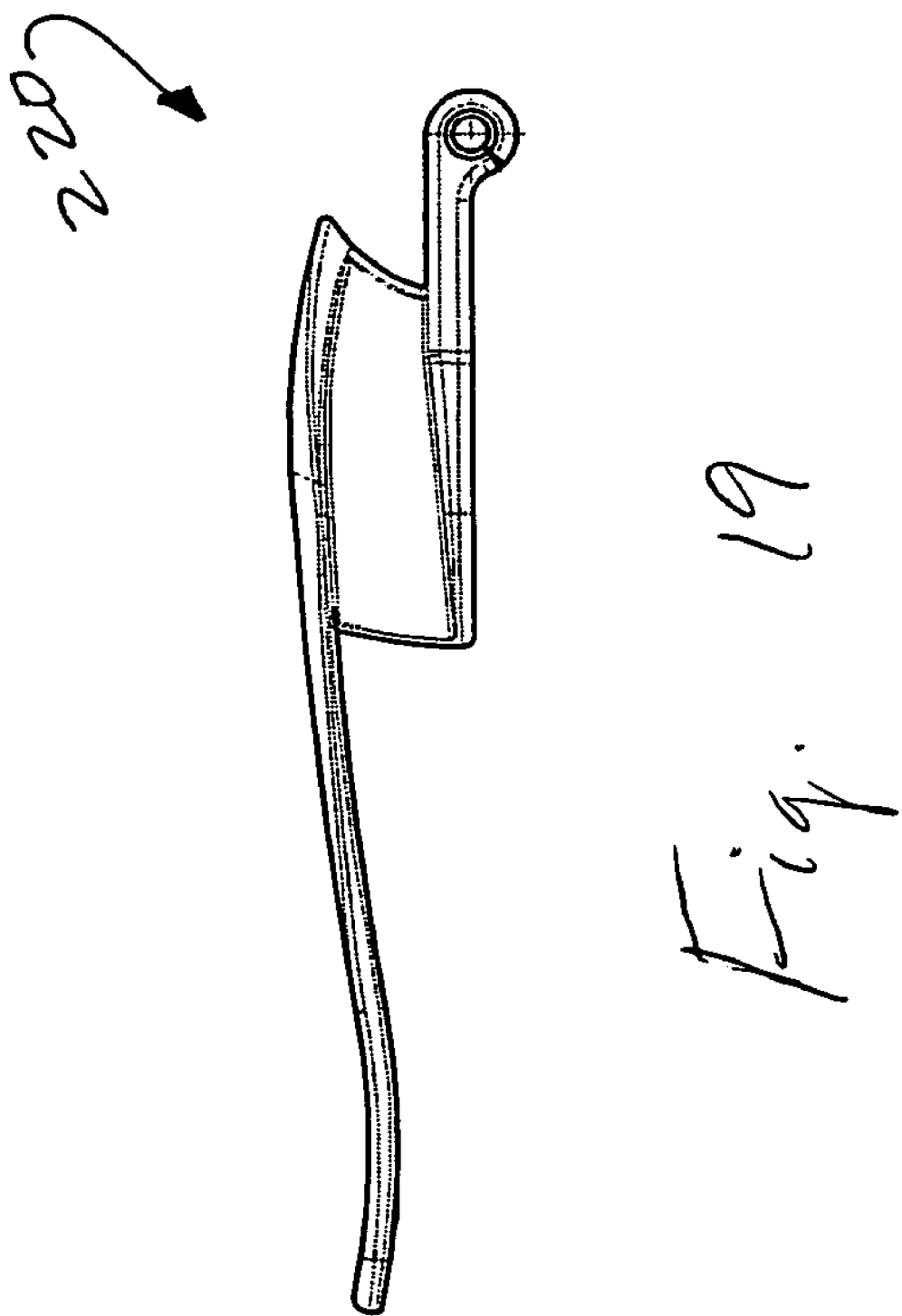
FIG. 19 is an enlarged elevation view of the actuator of the exemplary embodiment of FIG. 7.

Details of the actuator 220 are shown in FIG. 19. The actuator 220 is arranged to provide a mechanical advantage that reduces an amount of force required to break the ampoule 250. Further, the actuator 220 is designed to provide finer control in dispensing the adhesive or sealant material.

The applicator/dispenser 200 may be operated similarly to the first embodiment described above, rotating the valve sleeve 284 relative to the valve stem 282 to establish the desired communication as a three-way valve.

As noted above, the amount of adhesive or sealant material 252 may be prepackaged in the applicator/dispenser 200. The applicator/dispenser 200 may be disposable and discarded after the amount of adhesive or sealant material 252 in the frangible ampoule 240 has been dispensed or otherwise been used (i.e., polymerized). Alternatively, the amount of adhesive or sealant material 252 may be separate from the applicator/dispenser 200 and supplied to the applicator/dispenser 200 prior to use.

In embodiments, a user may be able to select from a variety of adhesive or sealant materials and/or amounts by selecting a frangible ampoule to be installed in the applicator/dispenser 200. For example, a kit may be provided that includes at least one applicator/dispenser 200 and a plurality of frangible ampoules 250. A plurality of detachable or replaceable tips may also be included in the kit.

Figure 20:
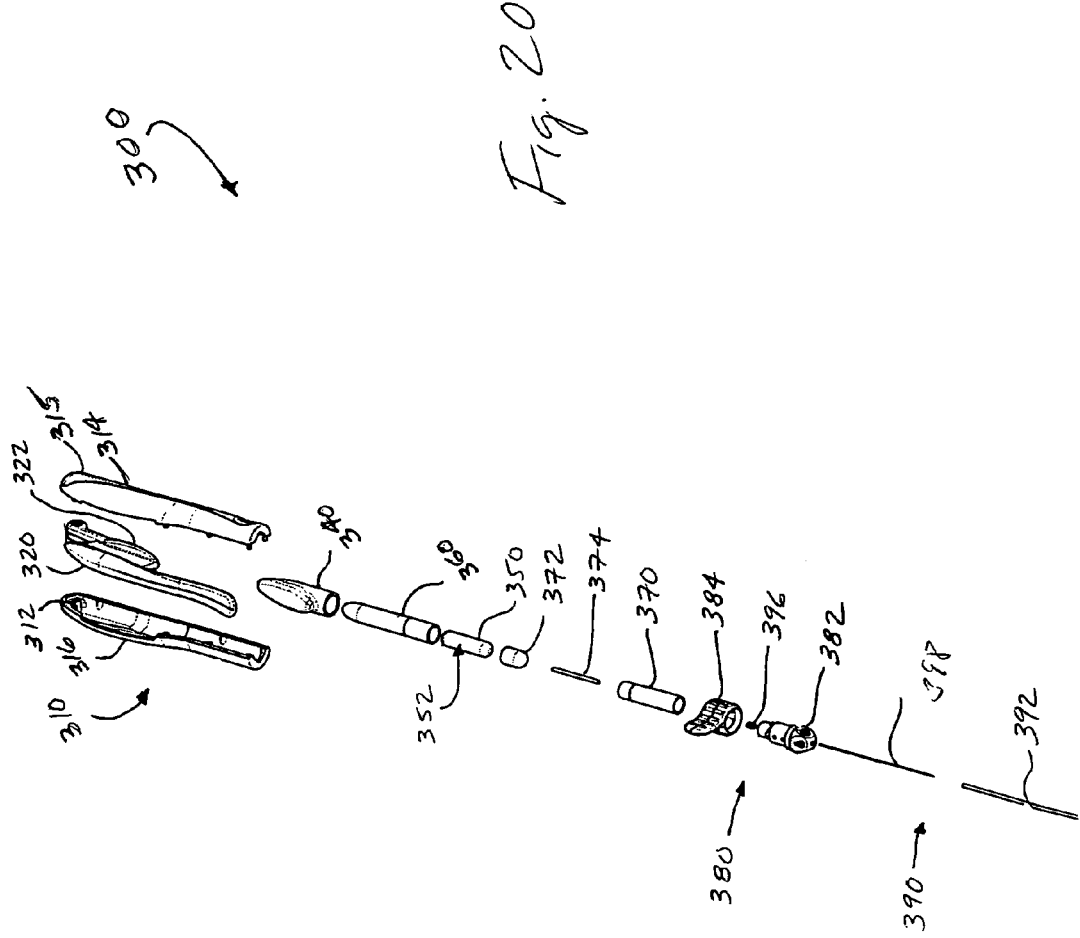
FIG. 20 is an exploded perspective view of a third exemplary embodiment of this invention.

FIGS. 20-29 illustrate a third embodiment of this invention, although this invention is in no way limited to the specific design depicted therein. As shown in FIG. 20, an applicator/dispenser 300 is formed by a body portion 310 and an actuator 320 that is movable relative to the body portion 310. For example, in the embodiment shown, a pivoting connection 312 is provided that allows the actuator 320 to be moved relative to the body portion 310.

As shown in FIG. 20, the body portion 310 may comprise a first body portion 314 and a second body portion 316 that are fitted together in a suitable manner. An outer portion 315 of the first and second body portions 314, 316 may be made of a softer material for comfort and/or grip of a user. The pivoting connection 312 may be defined by respective portions of the first and second body portions 314, 316. Further, a cavity may be defined in the body portion 310, for example, upon assembly of the first and second body portions 314, 316.

A piercing or breaking portion 322 may be defined on the actuator 320. Movement of the actuator 320 relative to the body portion 310 moves the piercing or breaking portion 322 into the cavity.

A bladder 340 may be fitted in the cavity. As shown in FIG. 20, the body portion 310 defines an opening through which the actuator 320 extends when the first and second body portions 314 and 316 are fitted together. The bladder 340 may be positioned, for example, in the vicinity of the opening such that a push button portion 342 of the bladder 340 is contacted by the actuator 320 when the actuator 320 is depressed toward the body portion 310. As explained below, the push button portion 342 may thus be depressed by a user to dispense a desired quantity of polymerizable adhesive or sealant material from the applicator/dispenser 300, for example, through a fixed, detachable or replaceable tip 390. A user may apply pressure on the push button portion 342 by depressing the actuator 320 while the applicator/dispenser 300 is held by the body portion 310 as a handle. For example, a user may hold the applicator/dispenser 300 as a pen and press the actuator 320 with an index finger. As further described below, the actuator 320 may also be depressed by a user to mix a polymerizable adhesive or sealant material with a second material prior to dispensing.

It should be understood that the fixed, detachable or replaceable tip 390 may have any desired configuration. As shown, the tip 390 comprises a tube 392 that may be attached or connected directly to a valve stem 382, described further below. The tip 390 may be designed to friction fit in a bore of the valve stem 382. The tip 390 may be selected for a particular application such as vascular surgery, and is not limited to the tube 392 shown. For example, the applicator tip may be a fibrous swab, a sponge swab, a foam swab, a brush, a spatula or the like. Any suitable tip, either known or hereafter developed, may be used with the applicators/dispensers according to this invention.

A frangible ampoule 350 containing an amount of adhesive or sealant material 352 is disposed in the bladder 340. As discussed above, the frangible ampoule 350 may be made of any suitable material, preferably a material that promotes stability and shelf-life of the adhesive or sealant material 352. At least the push button portion 342 of the bladder 340 is made of a flexible material. The bladder 340 may be made of a suitable rubber, silicone or plastic material, such as, for example, polyvinyl chloride, polyethylene, polyurethane, natural or nitril rubber, or any combination thereof.

Figure 21:
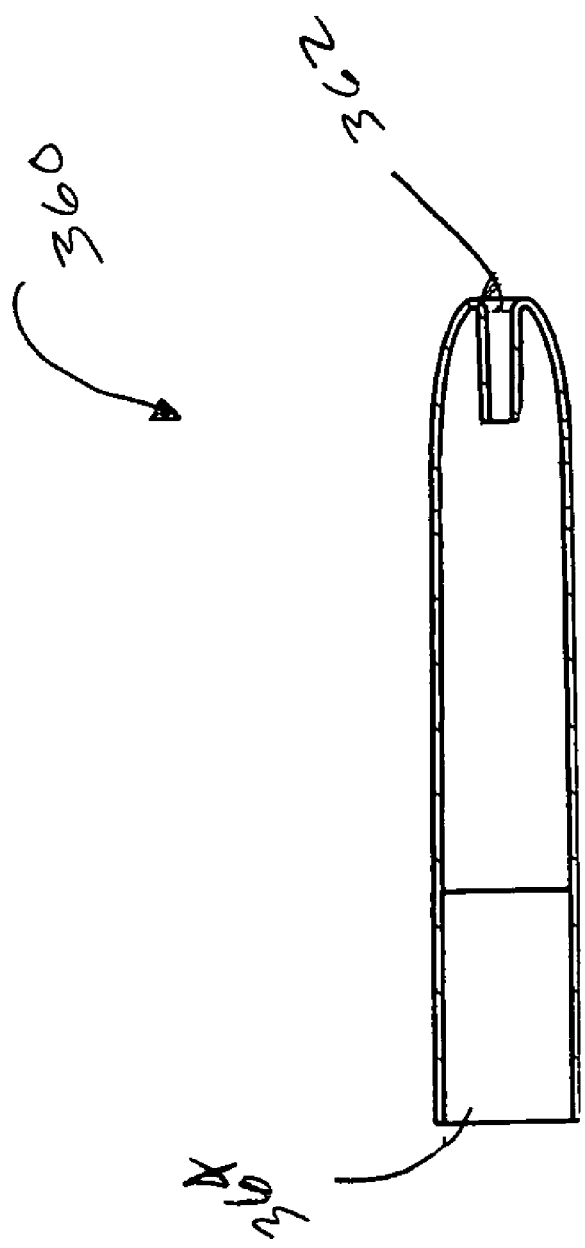
FIG. 21 is an enlarged cross-sectional view of the ampoule chamber of the exemplary embodiment of FIG. 20.

In the third embodiment, the ampoule 350 is surrounded by a second container 360, such as a tube, as shown in detail in FIG. 21. The second container 360 may be of any suitable material that is compatible with the particular adhesive or sealant to be applied, such as, for example, butyrate or polyethylene, and may be selected based on a desired application. Movement of the actuator 320 relative to the body portion 310 preferably moves the piercing or breaking portion 322 to rupture the ampoule 350 without breaking the second container 360.

As shown, the second container 360 has at least one hole 362 formed therein. When assembled, the second container 360 is positioned in the bladder 340 so that the hole 362 is placed in communication with the interior of the push button portion 342 of the bladder 340. As described below, this allows the depression of the push button portion 342 to apply pressure to expel the adhesive or sealant 352. In embodiments, the second container 360 is fixed or bonded to the bladder 340 so that the hole 362 is maintained in a proper position.

The second container 360 also has an open end 364 into which a porous plug 372 may be fitted, as illustrated in FIG. 20. The porous plug 372 may include a polymerization initiator or rate modifier for the polymerizable adhesive or sealant material to be dispensed. The porous plug 372 may be impregnated with the polymerization initiator or rate modifier, or may have the polymerization initiator or rate modifier coated on a surface thereof.

The bladder 340, the push button portion 342, the frangible ampoule 350, the second container 360 and the porous plug 372 may be assembled and inserted into the cavity of the body portion 310. Further, a second tube 370 may be disposed in the body portion 310 adjacent the porous plug 372.

Figure 22:
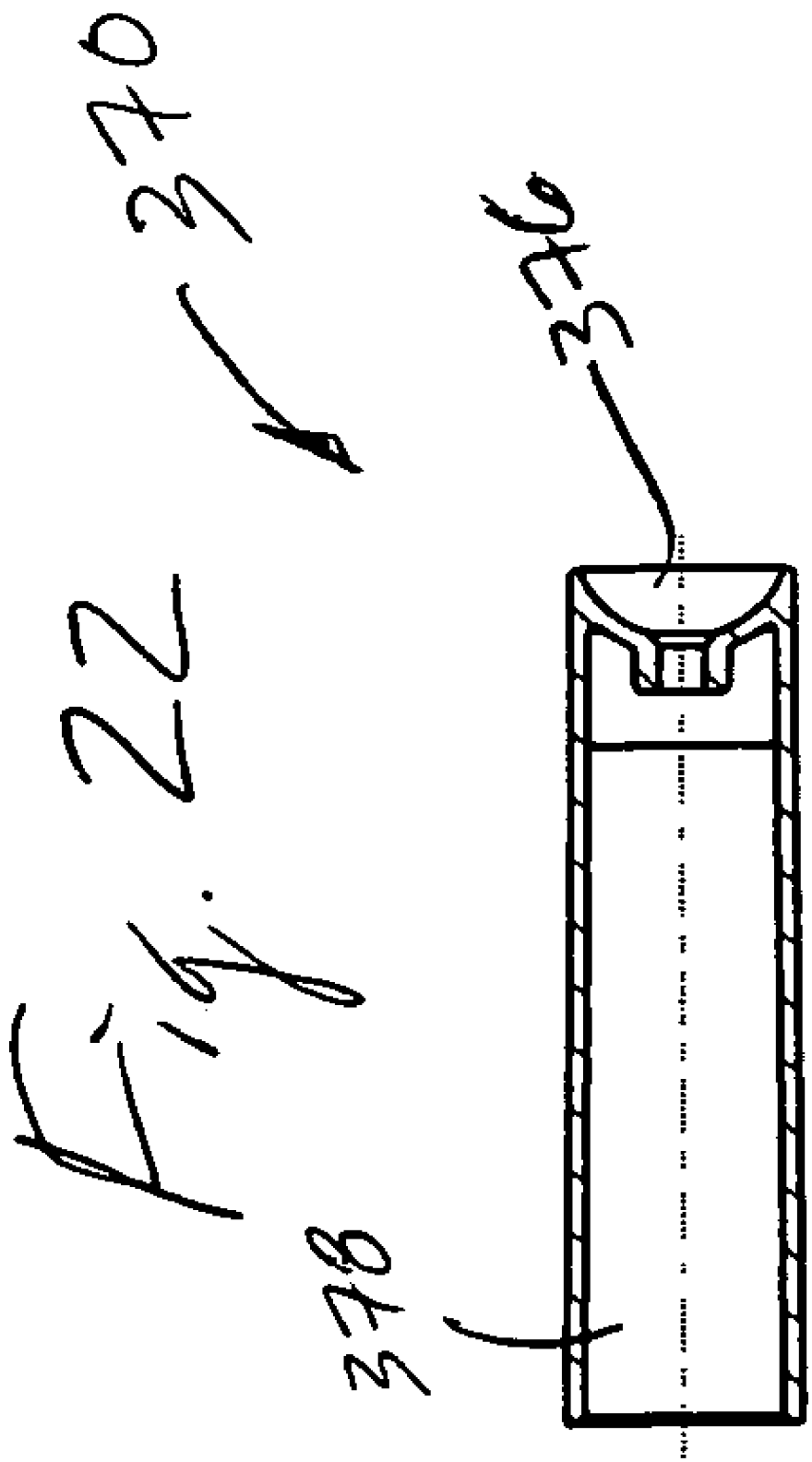
FIG. 22 is an enlarged cross-sectional view of the mixing chamber of the exemplary embodiment of FIG. 20.
Figure 23:
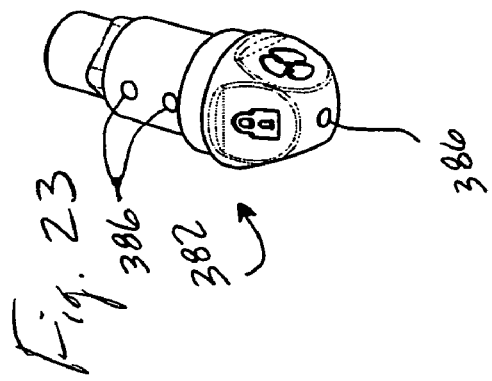
FIG. 23 is an enlarged perspective view of the valve stem of the exemplary embodiment of FIG. 20.
Figure 24:
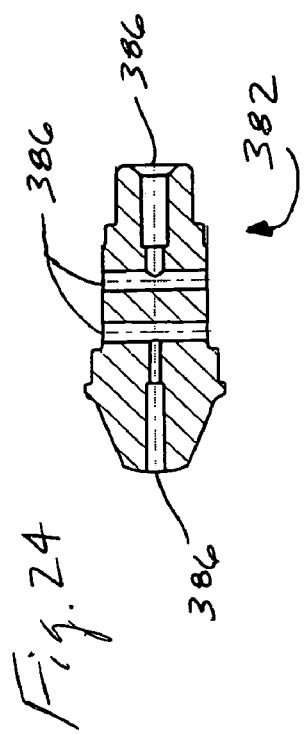
FIGS. 24-26 are enlarged cross-sectional views of the valve stem of FIG. 23.
Figure 25:
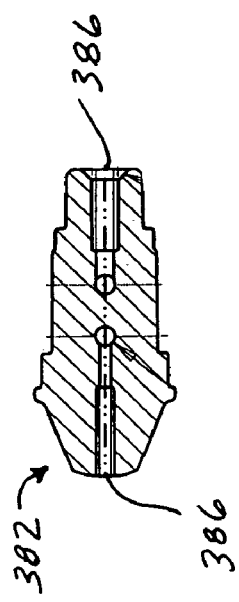
Figure 26:
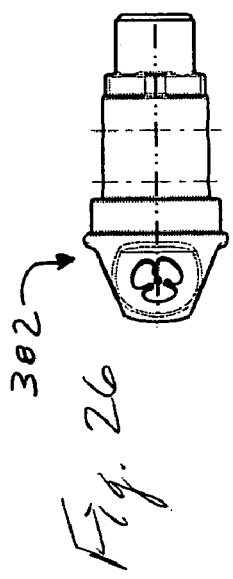

For example, as shown in FIG. 22, the second tube 370 may include a plug portion 376 that is configured to receive the porous plug 372. The second tube 370 may define a mixing chamber 378 which may be communicated with the plug portion 376 via a siphon tube 374 disposed in the second tube 370.

The applicator/dispenser 300 further includes a valve 380 that switches between an open state for communication between the bladder 340 and a dispensing opening that leads to the applicator tip 390, and a closed state. In the embodiment shown, the valve 380 comprises a first portion 382 and a second portion 384 movable relative to the first portion 382 to switch between the open and closed states. The first portion 382 may comprise a valve stem and the second portion 384 may comprise a valve sleeve that is rotatably mounted over a portion of the valve stem.

Figure 28:
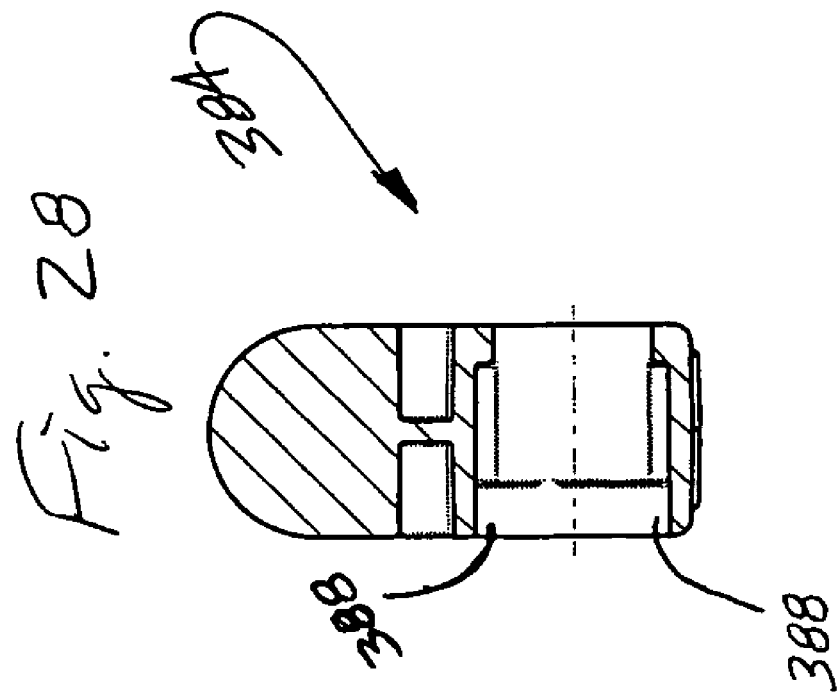
FIG. 28 is a cross-sectional view of the valve of FIG. 27.
Figure 27:
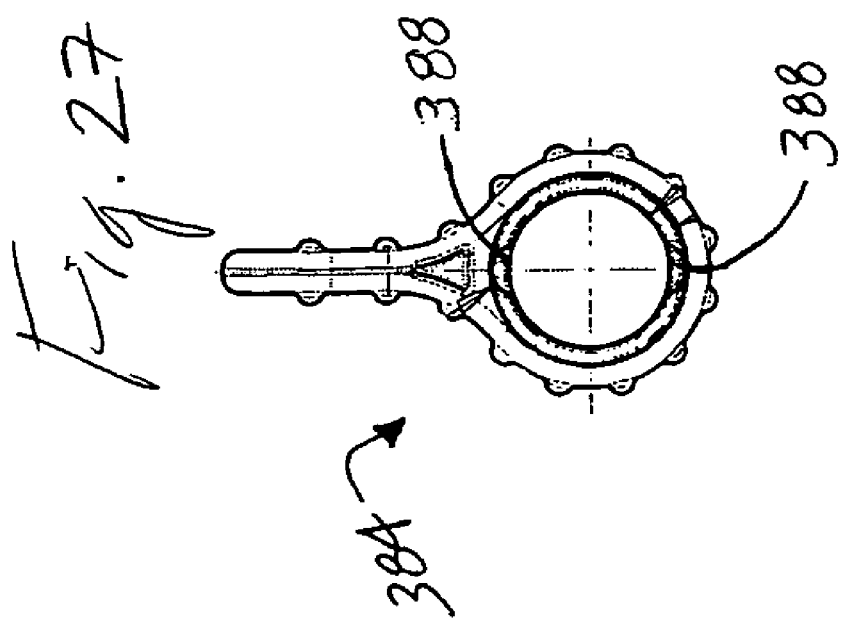
FIG. 27 is an enlarged axial view of the valve of the exemplary embodiment of FIG. 20.

The valve sleeve 384 may be rotated relative to the valve stem 382 to open/close a flow path through the valve 380. The flow path may be defined, for example, by a plurality of bores 386 formed in the valve stem 382 (see FIG. 24). Details of the valve stem 382 are shown in FIGS. 23-26. As the valve sleeve 384 is rotated relative to the valve stem 382, a cutout or groove 388 on an inner surface of the valve sleeve 384 is placed in communication with the plurality of bores 386. Details of the valve sleeve 384 are shown in FIGS. 27-28.

In the third embodiment, as in the second embodiment, a machined orifice 396 may be disposed in the valve stem 382, for example, in an end of the valve stem 382 adjacent to the mixing chamber 378. The machined orifice 396 is disposed between the cavity 330, i.e., the bladder 340, and the tip 390 to provide a restricted flow of a material when the material is being dispensed from the applicator/dispenser 300.

As shown in FIG. 20, the applicator/dispenser 300 may include a malleable wire 398. The malleable wire 398 may be disposed in the applicator tip 392, for example, as described above with respect to the second embodiment.

Figure 29:
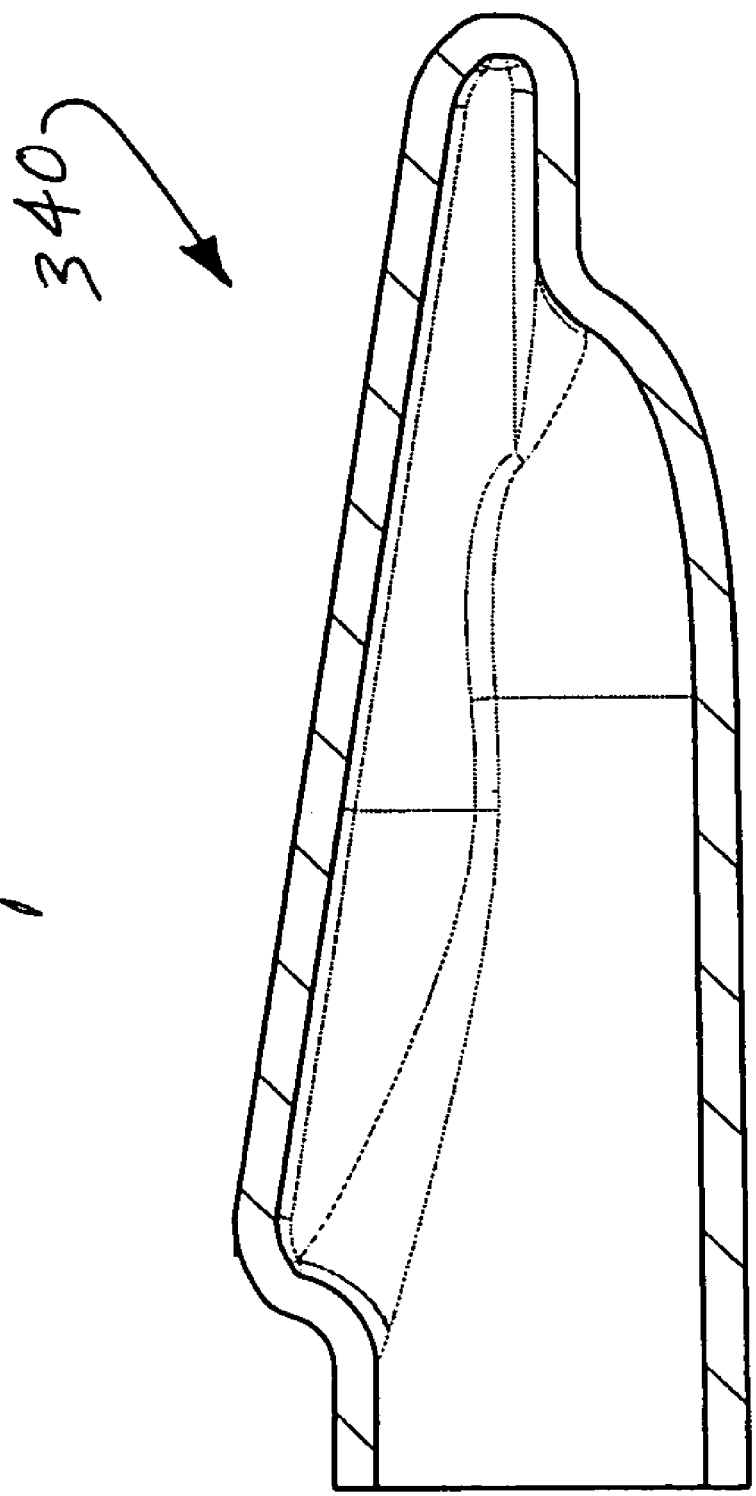
FIG. 29 is a cross-sectional view of the bladder of the exemplary embodiment of FIG. 20.

Details of the bladder 340 are shown in FIG. 29.

As described above, the applicator/dispenser 300 may be operated by rotating the valve sleeve 384 relative to the valve stem 382 to place the mixing chamber 378 and the applicator tip 392 in communication with one another.

As noted above, the amount of adhesive or sealant material 352 may be prepackaged in the applicator/dispenser 300. The applicator/dispenser 300 may be disposable and discarded after the amount of adhesive or sealant material 352 in the frangible ampoule 350 has been dispensed or otherwise been used (i.e., polymerized). Alternatively, the amount of adhesive or sealant material 352 may be separate from the applicator/dispenser 300 and supplied to the applicator/dispenser 300 prior to use.

In embodiments, a user may be able to select from a variety of adhesive or sealant materials and/or amounts by selecting a frangible ampoule to be installed in the applicator/dispenser 300. For example, a kit may be provided that includes at least one applicator/dispenser 300 and a plurality of frangible ampoules 350. A plurality of detachable or replaceable tips may also be included in the kit.

In embodiments, a user may be able to select from a variety of adhesive or sealant materials and/or amounts by selecting a frangible ampoule, a tube and/or bladder assembly (bladder, ampoule, tube and plug) to be installed in the applicator/dispenser 300. For example, a kit may be provided that includes at least one applicator/dispenser 300 and a plurality of frangible ampoules 350 (or bladder assemblies).

Figure 30:
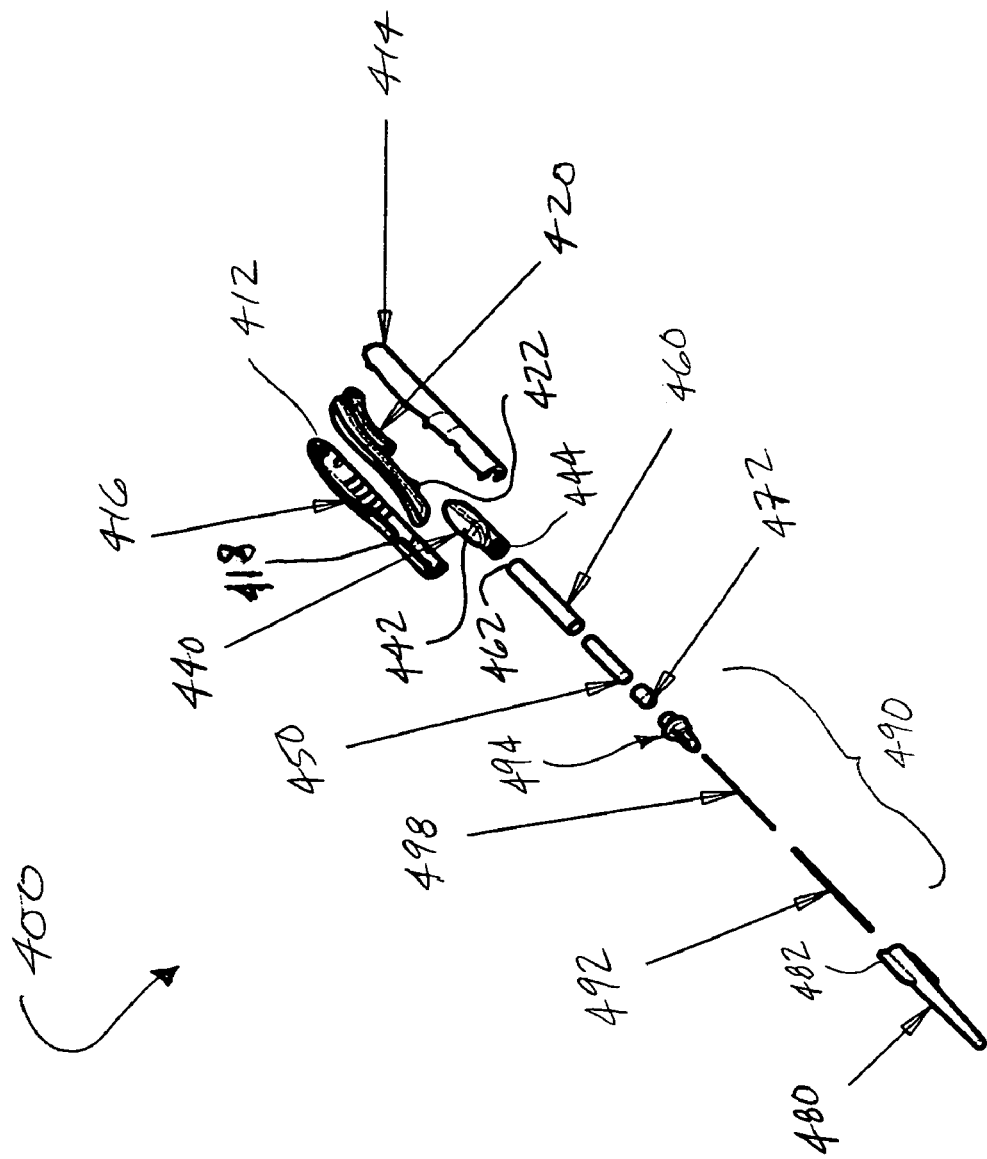
FIG. 30 is an exploded perspective view of a fourth exemplary embodiment of this invention.
Figure 31:
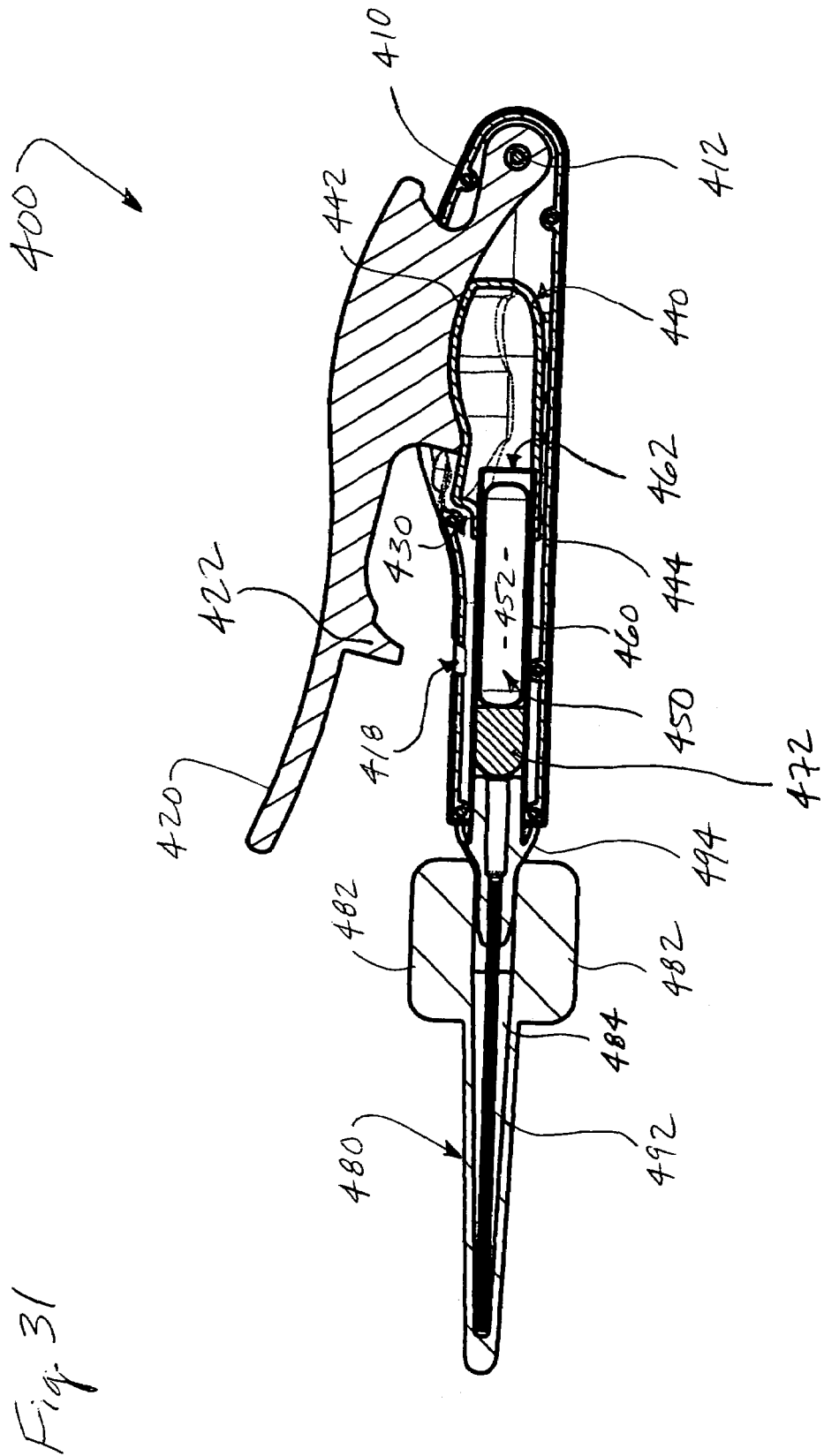
FIG. 31 is an enlarged cross-sectional view of the exemplary embodiment of FIG. 30.

FIGS. 30-31 illustrate a fourth embodiment of this invention, although this invention is in no way limited to the specific design depicted therein. As shown in FIGS. 30 and 31, an applicator/dispenser 400 is formed by a body portion 410 and an actuator 420 that is movable relative to the body portion 410. For example, in the embodiment shown, a pivoting connection 412 is provided that allows the actuator 420 to be moved relative to the body portion 410.

As shown in the exploded view of FIG. 30, the body portion 410 may comprise a first body portion 414 and a second body portion 416 that are fitted together in a suitable manner. The pivoting connection 412 may be defined by respective portions of the first and second body portions 414, 416. Further, a cavity 430 (shown in FIG. 31) may be defined in the body portion 410, for example, upon assembly of the first and second body portions 414, 416.

A piercing or breaking portion 422 may be defined on the actuator 420. Movement of the actuator 420 relative to the body portion 410 moves the piercing or breaking portion 422 into the cavity, for example, via a hole 418 in the body portion 410.

A bladder 440 may be fitted in the cavity 430. As shown in FIGS. 30 and 31, the body portion 410 has an opening through which the actuator 420 extends. The bladder 440 may be positioned such that a push button portion 442 of the bladder 440 is contacted by the actuator 420 when the actuator 420 is depressed toward the body portion 410. As explained below, the push button portion 442 may thus be depressed by a user to dispense a desired quantity of polymerizable adhesive or sealant material from the applicator/dispenser 400, for example, through a fixed, detachable or replaceable tip 490. A user may apply pressure on the push button portion 442 by depressing the actuator 420 while the applicator/dispenser 400 is held by the body portion 410 as a handle. For example, a user may hold the applicator/dispenser 400 as a pen and press the actuator 420 with an index finger. As further described below, the actuator 420 may also be depressed by a user to mix a polymerizable adhesive or sealant material with a second material prior to dispensing.

It should be understood that the fixed, detachable or replaceable tip 490 may have any desired configuration. As shown, the tip 490 comprises a tube 492 that may be attached or connected to the body portion 410, for example, by a connector 494. The tip 490 may be selected for a particular application such as vascular surgery, and is not limited to the tube 492 shown. For example, the applicator tip may be a fibrous swab, a sponge swab, a foam swab, a brush, a spatula or the like. Any suitable tip, either known or hereafter developed, may be used with the applicators/dispensers according to this invention. The tip 490 may be designed to friction fit over or within an end portion of the body portion 410.

A frangible ampoule 450 containing an amount of polymerizable adhesive or sealant 452 is disposed in the bladder 440. The frangible ampoule 450 may be made of any suitable material, preferably a material that promotes stability and shelf-life of the polymerizable adhesive or sealant material 452. For example, the frangible ampoule 450 may be made of glass. Other materials, such as, a plastic material or pierceable metal, such as aluminum, may be used for the frangible ampoule 450. An example of a suitable ampoule that can be used in the dispenser/applicators of the present invention is disclosed in, for example, U.S. Pat. No. 5,928,611, the entire disclosure of which is incorporated herein by reference. In fact, where such an ampoule is used in the present invention, the entire ampoule/applicator device may be used, which would thereby constitute not only the ampoule 450, but also a porous plug 472.

The porous plug 472 may include a polymerization initiator or rate modifier for the polymerizable adhesive or sealant material to be dispensed. The porous plug 472 may be impregnated with the polymerization initiator or rate modifier, or may have the polymerization initiator or rate modifier coated on a surface thereof.

In the fourth embodiment, the ampoule 450 is surrounded by a second container 460, such as a butyrate tube as shown. The second container 460 may be of any suitable material that is compatible with the particular adhesive or sealant to be applied, such as, for example, butyrate or polyethylene, and may be selected based on a desired application. Movement of the actuator 420 relative to the body portion 410 preferably moves the piercing or breaking portion 422 to rupture the ampoule 450 without breaking the second container 460.

The bladder 440 has an open end 444 into which at least part of the second container 460 is fitted. At least the push button portion 442 of the bladder 440 is made of a flexible material. The bladder 440 may be made of a suitable rubber, silicone or plastic material, such as, for example, polyvinyl chloride, polyethylene, polyurethane, natural or nitril rubber, or any combination thereof.

As shown, the second container 460 has at least one hole 462 formed therein. When assembled, the second container 460 is positioned in the bladder 440 so that the hole 462 is placed in communication with the interior of the push button portion 442 of the bladder 440, at least once the ampoule 450 is broken. As described below, this allows the depression of the push button portion 442 to apply pressure to expel the adhesive or sealant 452. In embodiments, the second container 460 is fixed or bonded to the bladder 440 so that the hole 462 is maintained in a proper position.

The bladder 440, the push button portion 442, the frangible ampoule 450, the second container 460 and the porous plug 472 may be assembled and inserted into the cavity 430 of the body portion 410, as shown in FIG. 31. The second container 460 may also surround the porous plug 472 and may receive an end of the connector 494 of the tip that extends into the body portion 410.

Further, the applicator/dispenser 400 may include a malleable wire 498, as shown in FIG. 30. The malleable wire 498 may be disposed in the applicator tip 492, for example, as described above with respect to the second embodiment.

The applicator/dispenser 400 further includes a cap 480 that is removably fitted over the applicator tip 490, as shown in FIG. 31. The cap 480 may include fins 482 that facilitate fixation of the cap 480 on and/or removal of the cap 480 from the applicator tip 490. While the cap 480 is shown as being removably fitted to the applicator tip 490, it should be understood that the cap 480 may also be removably fitted directly to the body portion 410.

With the cap 480 fitted in place over the applicator tip 490, the cap 480 defines a mixing chamber 484 that is in communication with the tube 492. When the ampoule 450 is broken to release the adhesive or sealant 452, the actuator 420 may be depressed to force the adhesive or sealant 452, through the porous plug 472 and the tube 492, into the mixing chamber 484. As the adhesive or sealant 452 passes through the porous plug 472, another material in or on the porous plug 472 may be added to the adhesive or sealant 452, as further described below.

In use, the actuator 420 is moved relative to the body portion 410 so that the piercing or breaking portion 422 is moved into the cavity 430 and breaks the ampoule 450 to release the adhesive or sealant material 452 into the second container 460 and/or the bladder 440.

When mixing of the adhesive or sealant material 452 is desired, for example, with a second material such as an initiator or polymerization rate modifier, the adhesive or sealant material 452 may be forced through the porous plug 472 and into the mixing chamber 484 of the cap 480 via the tube 492 by pressing the actuator 420 against the push button portion 442 of the bladder 440, applying pressure, displacing the adhesive or sealant material 452 and causing it to flow through the porous plug 472. The adhesive or sealant material 452 and the second material, contained by the porous plug 472, for example, are mixed in the mixing chamber 484 of the cap 480 and drawn back into the second container 460 by the tube 492 by depressing and releasing the actuator 420, for example, multiple times.

When dispensing of the adhesive or sealant material 452 is desired, the cap 480 may be removed so that a controlled flow of the adhesive or sealant material 452 may be obtained by depressing the actuator 420 against the push button portion 442 of the bladder 440 to a desired extent and/or a desired number of times. In embodiments, the volume displaced by depressing the push button portion 442 may correspond to a desired metered amount of the adhesive or sealant material 452 that is to be dispensed.

The amount of adhesive or sealant material 452 may be prepackaged in the applicator/dispenser 400. The applicator/dispenser 400 may be disposable and discarded after the amount of adhesive or sealant material 452 in the frangible ampoule 450 has been dispensed or otherwise been used (i.e., polymerized). Alternatively, the amount of adhesive or sealant material 452 may be separate from the applicator/dispenser 400 and supplied to the applicator/dispenser 400 prior to use.

In embodiments, a user may be able to select from a variety of adhesive or sealant materials and/or amounts by selecting a frangible ampoule and/or bladder assembly (bladder, ampoule and plug) to be installed in the applicator/dispenser 400.

For example, a kit may be provided that includes at least one applicator/dispenser 400 and a plurality of frangible ampoules 450 (or bladder assemblies). A plurality of detachable or replaceable tips 490 may also be included in the kit. The kit may also include a cleaning agent, such as isopropyl alcohol or other chemical sterilants, such as gluteraldehyde. Parts of the kit, such as the frangible ampoules 450 (or bladder assemblies) may be packaged separately, for example, in a blister pouch, and may be unpackaged and combined with the applicator/dispenser 400 as needed.

Figure 32:
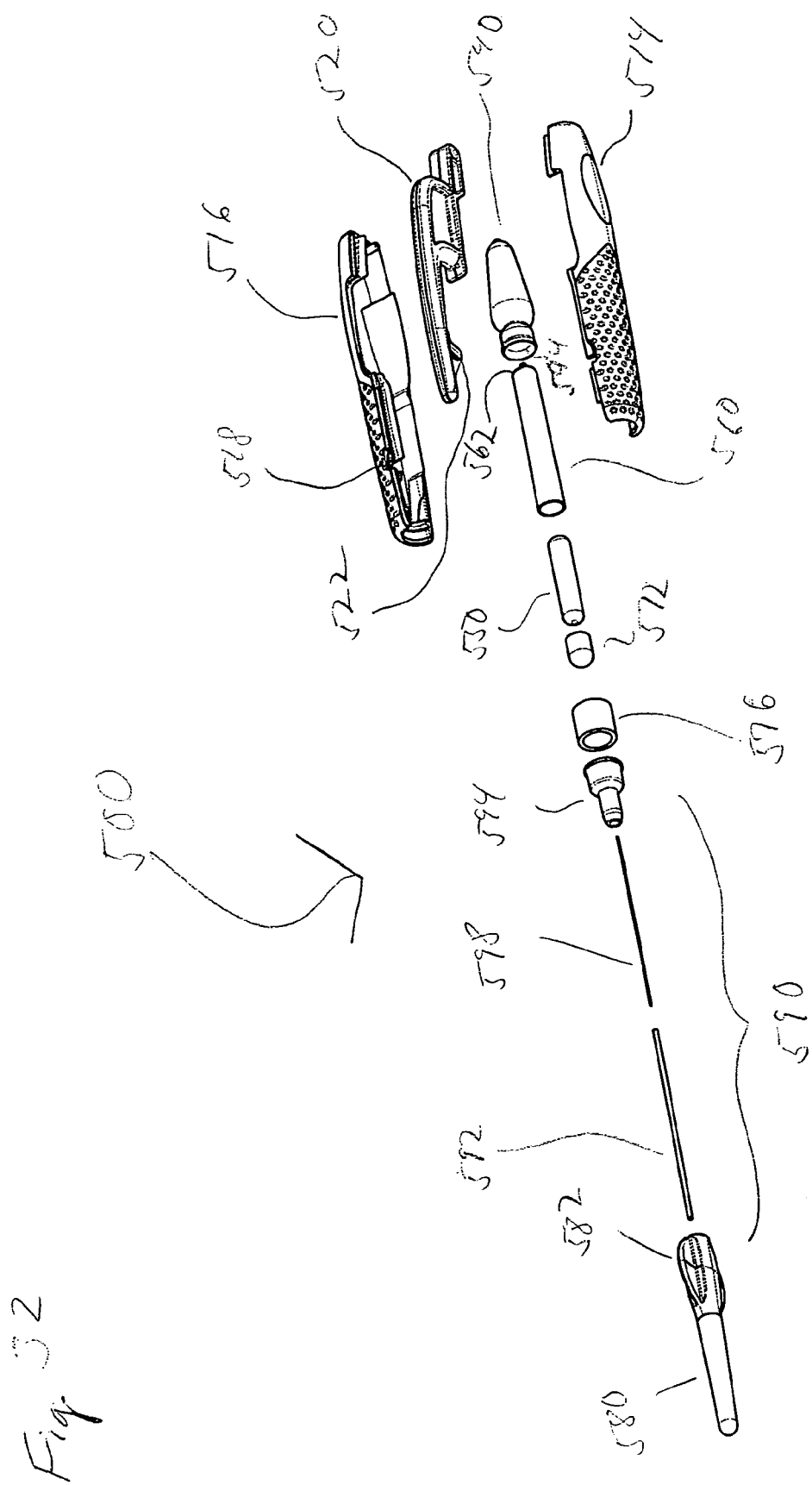
FIG. 32 is an exploded perspective view of a fifth exemplary embodiment of this invention.
Figure 33:
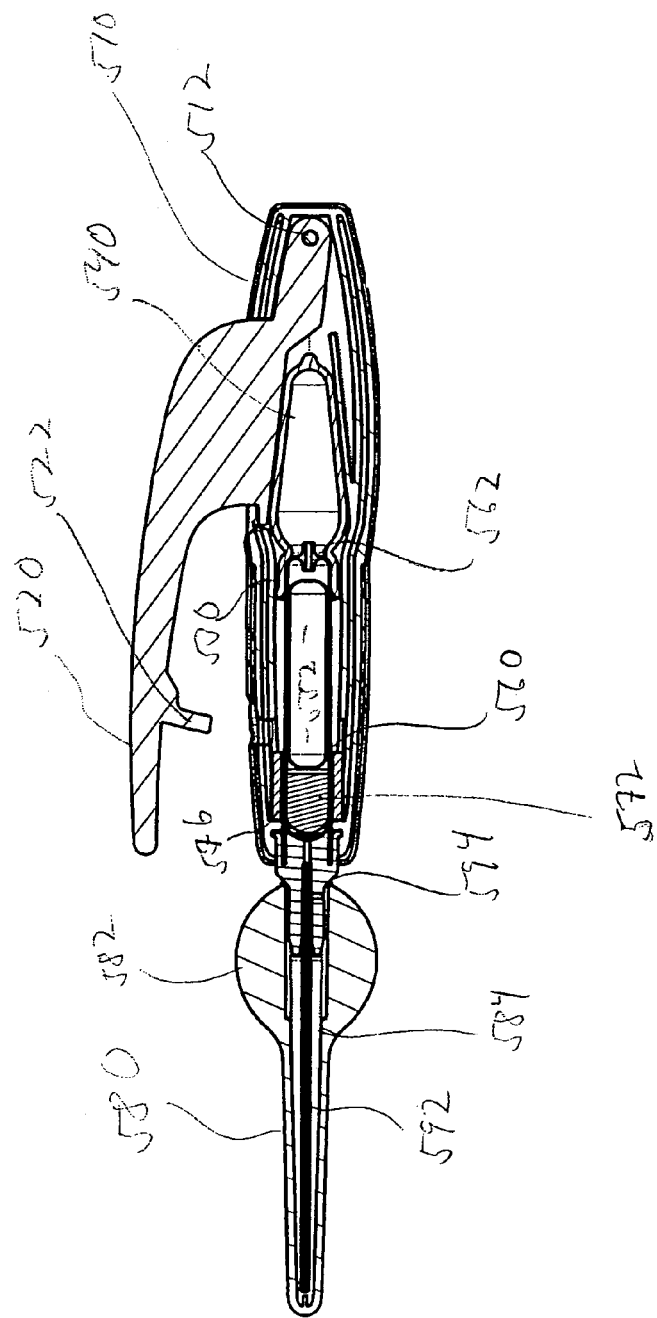
FIG. 33 is an enlarged cross-sectional view of the exemplary embodiment of FIG. 32.

FIGS. 32-33 illustrate a fifth embodiment of this invention, although this invention is in no way limited to the specific design depicted therein. As shown in FIGS. 32 and 33, an applicator/dispenser 500 is formed by a body portion 510 and an actuator 520 that is movable relative to the body portion 510. For example, in the embodiment shown, a pivoting connection 512 is provided that allows the actuator 520 to be moved relative to the body portion 510.

As shown in the exploded view of FIG. 32, the body portion 510 may comprise a first body portion 514 and a second body portion 516 that are fitted together in a suitable manner. The pivoting connection 512 may be defined by respective portions of the first and second body portions 514, 516. Further, a cavity 530 (shown in FIG. 33) may be defined in the body portion 510, for example, upon assembly of the first and second body portions 514, 516.

A piercing or breaking portion 522 may be defined on the actuator 520. Movement of the actuator 520 relative to the body portion 510 moves the piercing or breaking portion 522 into the cavity, for example, via a hole 518 in the body portion 510.

A bladder 540 may be fitted in the cavity 530. As shown in FIGS. 32 and 33, the body portion 510 has an opening through which the actuator 520 extends. The bladder 540 may be positioned such that the bladder 540 is contacted by the actuator 520 when the actuator 520 is depressed toward the body portion 510. As explained below, the bladder 540 may thus be depressed by a user to dispense a desired quantity of polymerizable adhesive or sealant material from the applicator/dispenser 500, for example, through a fixed, detachable or replaceable tip 590. A user may apply pressure on the bladder 540 by depressing the actuator 520 while the applicator/dispenser 500 is held by the body portion 510 as a handle. For example, a user may hold the applicator/dispenser 500 as a pen and press the actuator 520 with an index finger. As further described below, the actuator 520 may also be depressed by a user to mix a polymerizable adhesive or sealant material with a second material prior to dispensing.

It should be understood that the fixed, detachable or replaceable tip 590 may have any desired configuration. As shown, the tip 590 comprises a tube 592 that may be attached or connected to the body portion 510, for example, by a connector 594. The tip 590 may be selected for a particular application such as vascular surgery, and is not limited to the tube 592 shown. For example, the applicator tip may be a fibrous swab, a sponge swab, a foam swab, a brush, a spatula or the like. Any suitable tip, either known or hereafter developed, may be used with the applicators/dispensers according to this invention. The tip 590 may be designed to friction fit over or within an end portion of the body portion 510.

A frangible ampoule 550 containing an amount of polymerizable adhesive or sealant 552 is disposed in the bladder 540. The frangible ampoule 550 may be made of any suitable material, preferably a material that promotes stability and shelf-life of the polymerizable adhesive or sealant material 552. For example, the frangible ampoule 550 may be made of glass. Other materials, such as, a plastic material or pierceable metal, such as aluminum, may be used for the frangible ampoule 550. An example of a suitable ampoule that can be used in the dispenser/applicators of the present invention is disclosed in, for example, U.S. Pat. No. 5,928,611, the entire disclosure of which is incorporated herein by reference. In fact, where such an ampoule is used in the present invention, the entire ampoule/applicator device may be used, which would thereby constitute not only the ampoule 550, but also a porous plug 572.

The porous plug 572 may include a polymerization initiator or rate modifier for the polymerizable adhesive or sealant material to be dispensed. The porous plug 572 may be impregnated with the polymerization initiator or rate modifier, or may have the polymerization initiator or rate modifier coated on a surface thereof.

In the fifth embodiment, the ampoule 550 is surrounded by a second container 560, such as a butyrate tube as shown. The second container 560 may be of any suitable material that is compatible with the particular adhesive or sealant to be applied, such as, for example, butyrate or polyethylene, and may be selected based on a desired application. Movement of the actuator 520 relative to the body portion 510 preferably moves the piercing or breaking portion 522 to rupture the ampoule 550 without breaking the second container 560.

The bladder 540 has an open end 554 into which at least part of the second container 560 is fitted. The bladder 540 is made of a flexible material. For example, the bladder 540 may be made of a suitable rubber, silicone or plastic material, such as, for example, polyvinyl chloride, polyethylene, polyurethane, natural or nitril rubber, or any combination thereof.

As shown, the second container 560 has at least one hole 562 formed therein. When assembled, the second container 560 is positioned in the bladder 540 so that the hole 562 is placed in communication with the interior of the bladder 540, at least once the ampoule 550 is broken. As described below, this allows the depression of the bladder 540 to apply pressure to expel the adhesive or sealant 552. In embodiments, the second container 560 is fixed or bonded to the bladder 540 so that the hole 562 is maintained in a proper position.

The applicator/dispenser 500 further includes a collar 576 that is fitted over the second container 560 and provides mechanical protection against breakage of the ampoule 550 by the breaking portion 522 of the actuator 520. In an exemplary embodiment, the collar 576 may be comprised of stainless steel, or other suitable material. The collar 576 is slidably fitted over the second container 560 so that when the applicator/dispenser is in a "tip-up" position, the collar 576 prevents the breaking portion 522 of the actuator 520 from breaking or rupturing the ampoule 550. When the applicator/dispenser 500 is in a "tip-down" position, i.e., in a position for use, the collar 560 slides forward, thereby allowing the breaking portion 522 of the actuator 520 to come into contact with the ampoule 550. In this way, accidental or incidental breakage of the ampoule is prevented.

Although a collar 576 has been described as a device to prevent breakage of the ampoule, other devices such as a ball bearing, or other appropriate means are contemplated to be within a scope of this invention to act as a mechanical stop of the breaking portion 522.

The bladder 540, the frangible ampoule 550, the second container 560, the collar 576 and the porous plug 572 may be assembled and inserted into the cavity 530 of the body portion 510, as shown in FIG. 33. The second container 560 may also surround the porous plug 572 and may receive an end of the connector 594 of the tip that extends into the body portion 510.

Further, the applicator/dispenser 500 may include a malleable wire 598, as shown in FIG. 32. The malleable wire 598 may be disposed in the applicator tip 590, for example, as described above with respect to the second embodiment.

The applicator/dispenser 500 further includes a cap 580 that is removably fitted over the applicator tip 590, as shown in FIG. 33. The cap 580 may include fins 582 that facilitate fixation of the cap 580 on and/or removal of the cap 580 from the applicator tip 590. While the cap 580 is shown as being removably fitted to the applicator tip 590, it should be understood that the cap 580 may also be removably fitted directly to the body portion 510.

With the cap 580 fitted in place over the applicator tip 590, the cap 580 defines a mixing chamber 584 that is in communication with the tube 592. When the ampoule 550 is broken to release the adhesive or sealant 552, the actuator 520 may be depressed to force the adhesive or sealant 552, through the porous plug 572 and the tube 592, into the mixing chamber 584. As the adhesive or sealant 552 passes through the porous plug 572, another material in or on the porous plug 572 may be added to the adhesive or sealant 552, as further described below.

In use, the actuator 520 is moved relative to the body portion 510 so that the piercing or breaking portion 522 is moved into the cavity 530 and breaks the ampoule 550 to release the adhesive or sealant material 552 into the second container 560 and/or the bladder 540 when the applicator/dispenser 500 is in the tip-down position.

When mixing of the adhesive or sealant material 552 is desired, for example, with a second material such as an initiator or polymerization rate modifier, the adhesive or sealant material 552 may be forced through the porous plug 572 and into the mixing chamber 584 of the cap 580 via the tube 592 by pressing the actuator 520 against the push button portion 542 of the bladder 540, applying pressure, displacing the adhesive or sealant material 552 and causing it to flow through the porous plug 572. The adhesive or sealant material 552 and the second material, contained by the porous plug 572, for example, are mixed in the mixing chamber 584 of the cap 580 and drawn back into the second container 560 by the tube 592 by depressing and releasing the actuator 520, for example, multiple times.

When dispensing of the adhesive or sealant material 552 is desired, the cap 580 may be removed so that a controlled flow of the adhesive or sealant material 552 may be obtained by depressing the actuator 520 against the bladder 540 to a desired extent and/or a desired number of times. In embodiments, the volume displaced by depressing the bladder 540 may correspond to a desired metered amount of the adhesive or sealant material 552 that is to be dispensed.

The amount of adhesive or sealant material 552 may be prepackaged in the applicator/dispenser 500. The applicator/dispenser 500 may be disposable and discarded after the amount of adhesive or sealant material 552 in the frangible ampoule 550 has been dispensed or otherwise been used (i.e., polymerized). Alternatively, the amount of adhesive or sealant material 552 may be separate from the applicator/dispenser 500 and supplied to the applicator/dispenser 500 prior to use.

In embodiments, a user may be able to select from a variety of adhesive or sealant materials and/or amounts by selecting a frangible ampoule and/or bladder assembly (bladder, ampoule and plug) to be installed in the applicator/dispenser 500.

For example, a kit may be provided that includes at least one applicator/dispenser 500 and a plurality of frangible ampoules 550 (or bladder assemblies). A plurality of detachable or replaceable tips 590 may also be included in the kit. The kit may also include a cleaning agent, such as isopropyl alcohol or other chemical sterilants, such as gluteraldehyde. Parts of the kit, such as the frangible ampoules 550 (or bladder assemblies) may be packaged separately, for example, in a blister pouch, and may be unpackaged and combined with the applicator/dispenser 500 as needed.

Suitable applicator tips for the applicators/dispensers of this invention may include swabs, brushes, spatulas, droppers, syringes, and the like. Any suitable applicator tip can be used that allows for application of the adhesive or sealant composition to the desired site, and thus different applicator tips may be appropriate for different application methods. The applicator tip can have a variety of suitable shapes, including, but not limited to, conical, cylindrical, chisel or polygonal shapes such as rectangular or trapezoidal. The length and size of the tip can be varied depending on various application parameters. The tip may be detachable from the applicator body, or may be an integral part of the applicator.

The replaceable tip can be composed of any of a variety of materials including polymerized materials such as plastics, foams, rubber, thermosets, films, or membranes. Additionally, the replaceable tip may be composed of materials such as metal, glass, paper, ceramics, cardboard, and the like. The replaceable tip material may be porous, absorbent, or adsorbent in nature to enhance and facilitate application of the adhesive or sealant composition. In general, the only limitation on the materials used to fabricate the tip is that the tip must be sufficiently compatible with the composition to be dispensed that undesirable effects on the composition do not prevail during contact of the composition with the tip. Thus, for example, according to embodiments of this invention where the adhesive or sealant composition is packaged as already being absorbed or adsorbed into the tip, or in direct contact with the tip, the tip is preferably made from a material that tends to stabilize, or at least does not prematurely polymerize, the adhesive or sealant monomer composition. Where the tip is made from polymer materials, the polymer material can be the same as or different from those specified above. Suitable designs for tips that may be used according to this invention are disclosed in, for example, U.S. patent application Ser. No. 08/488,411, filed Jun. 7, 1995, Ser. No. 09/069,979, filed Apr. 30, 1998, Ser. No. 09/069,875, filed Apr. 30, 1998, and Ser. No. 09/385,030, filed Aug. 30, 1999, the entire disclosures of which are incorporated herein by reference.

Furthermore, the tips of the dispensers/applicators of this invention can be provided in any of various sizes, depending on the desired use of the product. For example, a standard preferred swab size can be a rectangular shape having a size of about 1.3 cm×1.0 cm×0.64 cm. However, larger or smaller sizes can be used, where the sizes are tailored to the shape of the tip and/or the amount of adhesive or sealant material to be applied for a given application. Thus, for example, where the dispenser/applicator is intended for applications requiring a large amount of adhesive or sealant material, a larger (and/or more absorbent) tip can be used; whereas where the dispenser/applicator is intended for applications requiring only a small amount of adhesive or sealant material, a smaller (and/or less absorbent) tip can be used. Tailoring the size or absorbency/adsorbency of the tip to the amount of adhesive or sealant required can help prevent waste of adhesive or sealant material. For example, where a large tip (and large amount of adhesive or sealant) is used for a small adhesive or sealant application, the remaining adhesive or sealant in the tip is generally wasted due to premature polymerization of the adhesive or sealant in the tip.

In addition to a polymerization initiator or rate modifier, the porous member may include a medicament, an anesthetic and/or other material to be applied.

The applicators/dispensers of this invention may be used to apply the polymerizable adhesive or sealant composition to a variety of substrates for the purposes of protecting, sealing, and bonding surfaces together. Suitable substrates include, but are not limited to, metals, plastics, rubbers, wood, ceramics, fabrics, cement, paper, living tissue and the like. For example, the polymerizable and/or cross-linkable material may be useful as tissue adhesive or sealants, sealants for preventing bleeding or for covering open wounds, systems for delivery of therapeutic or other bioactive agents, and other biomedical applications. They find uses in, for example, closing surgically incised or traumatically lacerated tissues; setting fractured bone structures; retarding blood flow from wounds; aiding repair and regrowth of living tissues; providing implantable matrixes for delivering bioactive agents; dressing burns; dressing skin or other superficial or surface wounds (such as abrasions, chaffed or raw skin, and/or stomatitis); protecting tissues prone to damage (e.g., as artificial calluses); and providing structural implants.

The adhesive or sealant material, in embodiments, is preferably a monomeric (including prepolymeric) adhesive or sealant composition. In embodiments, the monomer is a 1,1-disubstituted ethylene monomer, e.g., an α-cyanoacrylate. Preferred monomer compositions of this invention, and polymers formed therefrom, are useful as tissue adhesive or sealants, sealants for preventing bleeding or for covering open wounds, and in other absorbable and non-absorbable biomedical applications. They find uses in, for example, apposing surgically incised or traumatically lacerated tissues; retarding blood flow from wounds; drug delivery; dressing burns; dressing skin or other superficial or surface wounds (such as abrasions, chaffed or raw skin, and/or stomatitis); hernia repair; meniscus repair; and aiding repair and regrowth of living tissue. Other preferred monomer compositions of this invention, and polymers formed therefrom, are useful in industrial and home applications, for example in bonding rubbers, plastics, wood, composites, fabrics, and other natural and synthetic materials.

The monomer (including prepolymeric) adhesive or sealant composition may include one or more polymerizable monomers. Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. Nos. 5,328,687 and 5,928,611 to Leung et al., U.S. patent application Ser. No. 09/430,177, filed on Oct. 29, 1999, and U.S. Pat. No. 6,183,593, which are hereby incorporated in their entirety by reference herein. Preferred monomers include 1,1-disubstituted ethylene monomers, such as α-cyanoacrylates including, but not limited to, alkyl α-cyanoacrylates having an alkyl chain length of from about 1 to about 20 carbon atoms or more, preferably from about 2 to about 12 or more preferably from about 3 to about 8 carbon atoms. Other suitable monomers include, but are not limited to, alkyl ester cyanoacrylate monomers, such as those disclosed in, for example, U.S. patent applications Ser. No. 09/630,437, filed Aug. 2, 2000, and Ser. No. 09/919,877, filed Aug. 2, 2001, the entire disclosures of which are incorporated herein by reference.

The α-cyanoacrylates of this invention can be prepared according to several methods known in the art. U.S. Pat. Nos. 2,721,858, 3,254,111, 3,995,641, and 4,364,876, each of which is hereby incorporated in its entirety by reference herein, disclose methods for preparing α-cyanoacrylates.

As desired, the application according to this invention can include any of a wide variety of additional materials, either mixed into the polymerizable composition, or in a separate compartment from the polymerizable composition. Examples of suitable additional materials include, but are not limited to, plasticizing agents, thixotropic agents, thickeners, natural or synthetic rubbers, stabilizers, pH modifiers, bioactive agents, cross-linking agents, chain transfer agents, fibrous reinforcements, colorants, preservatives, formaldehyde reducing or scavenging agents, flavorants, perfumes, mixtures thereof, and the like.

The adhesive or sealant material may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), polymethylmethacrylate, polydimethylsiloxane, hexadimethylsilazane, isopropyl myristate, isopropyl palmitate, and others as listed in U.S. patent application Ser. No. 09/471,392 filed Dec. 23, 1999, the disclosure of which is incorporated in its entirety by reference herein.

The adhesive or sealant material may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. No. 4,720,513, and U.S. patent application Ser. No. 09/374,207 filed Aug. 12, 1999, the disclosures of which are hereby incorporated in their entireties by reference herein.

The adhesive or sealant material may optionally also include thickeners. Suitable thickeners may include poly (2-ethylhexyl methacrylate), poly(2-ethylhexyl acrylate) and others as listed in U.S. patent application Ser. No. 09/471,392 filed Dec. 23, 1999, and Ser. No. 09/374,207, filed Aug. 12, 1999, the disclosures of which are incorporated by reference herein in their entirety.

The adhesive or sealant material may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The adhesive or sealant material may optionally also include one or more stabilizers, preferably both at least one anionic vapor phase stabilizer and at least one anionic liquid phase stabilizer. The composition may optionally also include, in addition to or in place of the anionic stabilizers, at least one free radical stabilizer. These stabilizing agents may inhibit premature polymerization. Suitable anionic and free radical stabilizers may include those listed in U.S. patent application Ser. No. 09/471,392 filed on Dec. 23, 1999, and Ser. No. 09/099,457, filed Jun. 18, 1998, the disclosures of which are incorporated by reference herein in their entirety.

The adhesive or sealant material may also include pH modifiers to control the rate of degradation of the resulting polymer, as disclosed in U.S. patent application Ser. No. 08/714,288, filed Sep. 18, 1996, the entire disclosure of which is hereby incorporated by reference herein in its entirety.

Adhesive or sealant materials of this invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328, 687, 5,514,371, 5,514,372, 5,575,997, 5,582,834 and 5,624, 669, all to Leung et al., which are hereby incorporated herein by reference in their entireties.

To improve the cohesive strength of adhesive or sealants formed from the adhesive or sealant materials of this invention, difunctional monomeric cross-linking agents may be added to the monomer compositions of this invention. Such crosslinking agents are known. U.S. Pat. No. 3,940,362 to Overhults, which is hereby incorporated herein in its entirety by reference, discloses exemplary cross-linking agents.

The adhesive or sealant materials of this invention may further contain fibrous reinforcement and colorants such as dyes, pigments, and pigment dyes. Examples of suitable fibrous reinforcement include PGA microfibrils, collagen microfibrils, and others as described in U.S. patent application Ser. No. 09/471,392 filed on Dec. 23, 1999, the disclosure of which is incorporated by reference herein in its entirety.

The polymerizable adhesive or sealant materials useful in this invention may also further contain one or more preservatives, for prolonging the storage life of the composition. Suitable preservatives, and methods for selecting them and incorporating them into adhesive or sealant compositions, are disclosed in U.S. patent application Ser. No. 09/430,180, the entire disclosure of which is incorporated herein by reference.

In embodiments of this invention, the adhesive or sealant material and/or parts of the applicator/dispenser may contain additional materials such as a polymerization initiator, accelerator, rate-modifier, and/or cross-linking agent for initiating polymerization and/or cross-linking of the polymerizable monomer material. Such initiators, accelerators, rate-modifiers, and/or cross-linking agents can be included in the porous member, in the adhesive or sealant material, and/or elsewhere, as appropriate.

In embodiments of this invention, particularly where the adhesive or sealant material is not in contact with the porous member prior to use, it is possible to add additional components to the porous member, such as polymerization initiators and/or accelerators, anesthetic, medicament or the like, or even any of the various additives described above with respect to the polymerizable adhesive or sealant. This is advantageous, for example, where additional initiator or accelerator may be necessary to provide the desired cure rate of the adhesive or sealant once it is applied or where additional treatment is desired. Furthermore, this is advantageous in embodiments where additional stabilizers or polymerization inhibitors must be added to the adhesive or sealant composition in the assembly.

As used herein, a polymerization initiator is any material that causes a monomer composition applied to a substantially dry tissue (i.e., substantially in the absence of plasma or like tissue fluids) to polymerize in less than 300 seconds at ambient temperature, for example, at approximately 21-25° C. Preferably, the initiator causes the monomer composition to polymerize in less than 150 seconds at ambient temperature, more preferably within 60, 90 or 130 seconds. As used herein, a polymerization rate modifier is any material that changes the rate at which a polymerizable monomer would polymerize in the absence of that material. Preferably, the rate modifier accelerates the rate of the polymerization reaction, although for particularly fast-acting monomers it may decelerate that rate.

The material may be applied to the porous member or other part of the applicator, for example, by spraying, dipping, injecting, or brushing the part tip with a liquid medium containing the polymerization initiator or accelerator. It is preferably applied to the part by dipping or injecting. For example, it may be applied to the part by pumping of the liquid medium, for example, through a syringe, onto the part. Methods of applying the polymerization initiator or accelerator to an applicator part are described in more detail in U.S. Pat. No. 5,928,611 to Leung and U.S. patent application Ser. No. 09/069,979, filed Apr. 30, 1998, Ser. No. 08/920,876, filed Aug. 29, 1997, and Ser. No. 09/430,177, filed Oct. 29, 1999, the entire disclosures of which is incorporated herein by reference.

Particular initiators and accelerators for particular monomers may be readily selected by one of skill in the art without undue experimentation. Control of the molecular weight distribution of the applied adhesive or sealant can be enhanced by selection of the concentration and functionality of the initiator or accelerator vis-a-vis the selected monomer. Suitable polymerization initiators and accelerators for cyanoacrylate compositions include, but are not limited to, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

In preferred embodiments, the initiator may be a bioactive material, including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt napthenate can be used as an accelerator for peroxide. Other suitable bioactive materials are disclosed in U.S. Pat. No. 5,928,611 to Leung and U.S. patent application Ser. No. 08/920,876, filed Aug. 29, 1997, Ser. No. 09/430,176 filed Oct. 29, 1999, and Ser. No. 09/430,177, filed Oct. 29, 1999, the entire disclosures of which is incorporated herein by reference.

The adhesive or sealant materials in this invention can also comprise a medicament. Inclusion of a medicament is often desirable in compositions intended for medical applications. The medicament can either be added to the monomer-containing adhesive or sealant composition prior to packaging, or, alternatively, to the porous member or other part. Thus, the medicament may be applied to a tissue prior to or simultaneously with application of the monomer-containing adhesive or sealant composition. In addition to serving its medicinal function, the medicament may be selected so that it functions in conjunction with the co-packaged polymerizable monomer composition to initiate polymerization of the monomer or modify (e.g., accelerate) the rate of polymerization for the monomer to form a polymeric adhesive or sealant. The proper combination of medicament and polymerizable monomer can be determined easily by one of skill in the art. The medicament is supplied in an amount that will be pharmaceutically effective when applied topically (i.e., directly to tissue).

Examples of such medicaments include, but are not limited to antibiotics, antimicrobials, antiseptics, bacteriocins, bacteriostats, disinfectants, steroids, anesthetics, fungicides, anti-inflammatory agents, antibacterial agents, antiviral agents, antitumor agents, growth promoters, and mixtures thereof.

Exemplary medicaments include, but are not limited to, quaternary ammonium halides such as benzalkonium chloride and benzethonium chloride; chlorhexidine sulfate; gentamicin sulfate; hydrogen peroxide; quinolone thioureas; silver salts, including, but not limited to, silver acetate, silver benzoate, silver carbonate, silver chloride, silver citrate, silver iodide, silver nitrate, and silver sulfate; sodium hypochlorite; salts of sulfadiazine, including, but not limited to silver, sodium, and zinc salts; and mixtures thereof.

Preferable medicaments are those that are anions or help in radical generation or that are ion pairs or are themselves radicals.

In embodiments, the medicament is preferably a quaternary ammonium halide such as alkylbenzyldimethylammonium chloride (benzalkonium chloride; BAC) with an alkyl containing 6-18 carbon atoms, its pure components, or mixtures thereof, or benzethonium chloride; or a salt of sulfadiazine, such as a silver, sodium, or zinc salt.

The medicament can have a pharmaceutical effect only at the site of application (i.e., limited to the tissue on/in which it is applied), or it can have a systemic effect (by systemic, it is not only meant that the medicament has an effect throughout the patient's body, but also at a specific site other than the site of application). In embodiments where the medicament is applied in an amount sufficient to show a systemic pharmaceutical activity, it can be absorbed, transported, or otherwise distributed to the site or sites within the patient where the pharmaceutical activity is desired, e.g., through the cardiovascular or lymph systems. The medicament may be in the form of a solid, such as a powder or a solid film, or in the form of a liquid, such as a watery, viscous, or paste-like material. The medicament may also be compounded with a variety of additives, such as surfactants or emulsifiers, and vehicles.

The polymerizable and/or cross-linkable material may be neat (no additional compounds added) or in a solvent, emulsion or suspension. Suitable solvents according to this invention include alcohol, ether alcohol, hydrocarbons, halogenated hydrocarbons, ethers, acetals, ketones, esters, acids, sulfur- or nitrogen-containing organic compounds, mixtures thereof and the like. Other suitable solvents are disclosed in U.S. Pat. No. 5,130,369 to Hughes et al. and U.S. Pat. No. 5,216,096 to Hattori et al., the entire disclosures of which are incorporated herein by reference. These solvents may be used either independently or in combination of two or more. They may also be used in conjunction with water to the extent that the polymerizable and/or cross-linkable material is dissolved or suspended in such a mixture. The total amount of solvent that may be incorporated into the polymerizable and/or cross-linkable material may be 0 to 99, preferably 1 to 50, and more preferably 3 to 25 percent by weight. Selection of the amount will, of course, depend on the desired monomer and process conditions, and amounts outside these ranges may be acceptable.

In embodiments, the monomer composition and/or its packaging are preferably sterilized. Sterilization of the monomer composition and/or its packaging can be accomplished by techniques known to one of ordinary skill in the art, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. patent application Ser. No. 09/025,472, filed on Feb. 18, 1998, the entire disclosure of which is incorporated herein by reference. The composition must show low levels of toxicity to living tissue during its useful life. In preferred embodiments of this invention, the composition is sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$. Further details of sterilization are disclosed in incorporated U.S. patent application Ser. No. 09/874,039.

It should be understood that the individual features of the various exemplary embodiments may be included or excluded as desired for a given application. As such, all possible combinations of the described features are considered to be encompassed by this invention.

Thus, while this invention has been described in terms of exemplary embodiments, it is to be understood that this invention is not to be limited to the particular configuration of these embodiments. Various modifications and/or alterations of these embodiments may be made while remaining within the scope of this invention.

What is claimed is:

1. An applicator/dispenser for dispensing, mixing and/or applying a polymerizable monomeric adhesive or sealant material, comprising:
   a body portion;
   an actuator movable relative to the body portion;
   a cavity in the body portion;
   a mixing chamber that communicates with the cavity;
   a bladder coupled to the actuator for providing back and forth communication between the cavity and the mixing chamber, said bladder is closed on one end and disposed at least partially within the cavity, at least a portion of the bladder being flexible;
   a flow regulating portion;
   a dispensing opening that communicates with at least one of the cavity and the mixing chamber;
   a valve that selectively establishes communication between at least two of:
   the cavity and the mixing chamber;
   the cavity and the dispensing opening; and
   the cavity, the mixing chamber and the dispensing opening; and
   a piercing or breaking portion on the actuator,
   wherein movement of the actuator relative to the body portion moves the piercing or breaking portion into the cavity, and wherein said repeated actuator movement provides for mixing of polymerizable monomeric adhesive or sealant material prior to dispensing.

2. The applicator/dispenser according to claim 1, wherein movement of the actuator relative to the body portion to move the piercing or breaking portion into the cavity is inhibited prior to use of the applicator/dispenser.

3. The applicator/dispenser according to claim 2, wherein the movement of the actuator relative to the body portion to move the piercing or breaking portion into the cavity is inhibited by a mechanical stop.

4. The applicator/dispenser according to claim 3, wherein the mechanical stop moves to a position to allow the movement of the actuator relative to the body portion to move the piercing or breaking portion into the cavity when the applicator/dispenser is oriented in a position to expel adhesive or sealant material.

5. An applicator/dispenser for dispensing, mixing and/or applying a polymerizable monomeric adhesive or sealant material, comprising:
   a body portion;
   an actuator movable relative to the body portion;
   a cavity in the body portion;
   a mixing chamber that communicates with the cavity;
   a bladder coupled to the actuator for providing back and forth communication between the cavity and the mixing chamber, said bladder is closed on one end and disposed at least partially within the cavity, at least a portion of the bladder being flexible;
   a flow regulating portion; and
   a piercing or breaking portion on the actuator,
   wherein movement of the actuator relative to the body portion moves the piercing or breaking portion into the cavity, and is inhibited by a mechanical stop comprising one of a collar and a bearing prior to use of the applicator/dispenser, and wherein said repeated actuator movement provides for mixing of polymerizable monomeric adhesive or sealant material prior to dispensing.

6. The applicator/dispenser according to claim 5, wherein the collar is slidably positioned in the cavity.

7. The applicator/dispenser according to claim 1, wherein the actuator comprises a lever movably mounted on the body portion.

8. The applicator/dispenser according to claim 1, further comprising a container of adhesive or sealant material at least partially disposed within the cavity, wherein movement of the actuator relative to the body portion moves the piercing or breaking portion to rupture the container.

9. The applicator/dispenser according to claim 8, wherein the adhesive or sealant material comprises a polymerizable monomer adhesive or sealant material.

10. The applicator/dispenser according to claim 8, wherein the adhesive or sealant material comprises a polymerizable 1,1-disubstitutedethylene monomer formulation.

11. The applicator/dispenser according to claim 8, wherein the adhesive or sealant material comprises a cyanoacrylate formulation.

12. The applicator/dispenser according to claim 8, further comprising a second container having at least one opening, the second container at least partially surrounding the container of adhesive or sealant, wherein movement of the actuator relative to the body portion moves the piercing or breaking portion to rupture the container containing the adhesive or sealant without breaking the second container.

13. The applicator/dispenser according to claim 12, wherein the second container includes an open hole.

14. The applicator/dispenser according to claim 12, wherein the second container completely surrounds the container of adhesive or sealant.

15. The applicator/dispenser according to claim 12, further comprising a plug member at least partially disposed in an opening of the second container, the plug member being made of a material that is at least one of porous, absorbent and adsorbent in nature.

16. The applicator/dispenser according to claim 15, wherein at least one of a medicament, a polymerization initiator, a polymerization rate modifier and a stabilizer for a polymerizable monomer is in or on the plug member.

17. The applicator/dispenser according to claim 12, wherein the container is formed from a material that stabilizes the polymerizable monomeric adhesive or sealant material.

18. The applicator/dispenser according to claim 1, wherein at least a part of the body portion defining the cavity is formed from a material that stabilizes a polymerizable monomeric adhesive or sealant material.

19. The applicator/dispenser according to claim 18, wherein the material that stabilizes a polymerizable monomeric adhesive or sealant material is a halogenated polymeric material.

20. The applicator/dispenser according to claim 19, wherein the halogenated polymeric material is selected from the group consisting of polyolefins, halogenated hydrocarbons, and engineered resins.

21. The applicator/dispenser according to claim 19, wherein the halogenated polymeric material is a fluorinated polymeric material.

22. The applicator/dispenser according to claim 1, wherein at least an inner surface of the cavity is coated with a material that stabilizes a polymerizable monomeric adhesive or sealant material.

23. The applicator/dispenser according to claim 1, wherein at least an inner surface of the cavity is impregnated with a material that stabilizes a polymerizable monomeric adhesive or sealant material.

24. The applicator/dispenser according to claim 1, further comprising a pivoting connection that movably connects the actuator and the body portion.

25. The applicator/dispenser according to claim 24, wherein the body portion comprises a handle portion of the applicator/dispenser.

26. The applicator/dispenser according to claim 1, further comprising a plug member at least partially disposed in an opening of the bladder, the plug member being made of a material that is at least one of porous, absorbent and adsorbent in nature.

27. The applicator/dispenser according to claim 26, wherein at least one of a medicament, a polymerization initiator, a polymerization rate modifier and a stabilizer for a polymerizable monomer is in or on the plug member.

28. The applicator/dispenser according to claim 1, further comprising:
 a container of adhesive or sealant material disposed at least partially located in the bladder, wherein movement of the actuator relative to the body portion moves the piercing or breaking portion to rupture the container.

29. The applicator/dispenser according to claim 28, further comprising a plug member at least partially disposed between the bladder and a dispensing opening, the plug member being made of a material that is at least one of porous, absorbent and adsorbent in nature.

30. The applicator/dispenser according to claim 29, wherein at least one of a medicament, a polymerization initiator, a polymerization rate modifier and a stabilizer for a polymerizable monomer is in or on the plug member.

31. The applicator/dispenser according to claim 1, wherein the mixing chamber comprises a cap removably fitted to the body portion.

32. The applicator/dispenser according to claim 1, wherein the valve, comprises:
 a first portion; and
 a second portion movable relative to the first portion to selectively establish communication between at least two of:
 the cavity and the mixing chamber;
 the cavity and the dispensing opening; and
 the cavity, the mixing chamber and the dispensing opening.

33. The applicator/dispenser according to claim 32, wherein the first portion comprises a valve stem, the second portion comprises a valve sleeve rotatably mounted over a portion of the valve stem, and rotation of the valve sleeve relative to the valve stem establishes different flow paths through the valve.

34. The applicator/dispenser according to claim 32, wherein the second portion inhibits movement of the actuator when the second portion is in a predetermined position.

35. The applicator/dispenser according to claim 1, further comprising an applicator/dispenser tip that is attached to at least one of the valve and the body portion.

36. The applicator/dispenser according to claim 35, wherein the applicator/dispenser tip comprises one of a tube, a nozzle, a spatula, a rolling ball, a brush, and a swab.

37. The applicator/dispenser according to claim 35, wherein the applicator/dispenser tip is removable.

38. The applicator/dispenser according to claim 35, further comprising a machined orifice disposed between the cavity and the applicator/dispenser tip, the machined orifice providing a restricted flow of a material when the material is being dispensed from the applicator/dispenser.

39. The applicator/dispenser according to claim 35, wherein the applicator/dispenser tip is malleably positionable.

40. The applicator/dispenser according to claim 1, further comprising an applicator/dispenser tip that is connected to the body portion.

41. The applicator/dispenser according to claim 40, wherein the applicator/dispenser tip comprises one of a tube, a nozzle, a spatula, a rolling ball, a brush, and a swab.

42. The applicator/dispenser according to claim 40, wherein the applicator/dispenser tip is removable.

43. The applicator/dispenser according to claim 40, further comprising a machined orifice disposed between the cavity and the applicator/dispenser tip, the machined orifice providing a restricted flow of a material when the material is being dispensed from the applicator/dispenser.

44. A kit comprising:
 at least one applicator/dispenser of claim 1; and
 a plurality of containers of adhesive or sealant material arranged to be placed at least partially in the cavity of the at least one applicator/dispenser, wherein movement of the actuator relative to the body portion moves the piercing or breaking portion to rupture one of the containers that is placed at least partially in the cavity.

45. The kit according to claim 44, further comprising a plurality of removable applicator tips.

46. The kit according to claim 44, further comprising a polymerization initiator or rate modifier for the adhesive or sealant material.

47. The kit according to claim 44, wherein the adhesive or sealant material comprises a polymerizable monomer adhesive or sealant material.

48. The kit according to claim 44, wherein the adhesive or sealant material comprises a polymerizable 1,1-disubstituted ethylene monomer formulation.

49. The kit according to claim 44, wherein the adhesive or sealant material comprises a cyanoacrylate formulation.

50. The kit according to claim 44, wherein at least two of the plurality of containers contain different amounts of adhesive or sealant material.

51. The kit according to claim 42, wherein at least two of the plurality of containers contain a different adhesive or sealant material.

52. A method of applying/dispensing an adhesive or sealant material, comprising:
 placing a container of adhesive or sealant material at least partially into the cavity of an applicator/dispenser according to claim 1;
 moving the actuator relative to the body portion to move the piercing or breaking portion to rupture the container; and
 dispensing the adhesive or sealant material from the applicator/dispenser.

53. The method of claim 52, further comprising applying the dispensed adhesive or sealant material to a substrate to be bonded.

54. The method of claim 53, wherein the substrate to be bonded is tissue.

55. The method of claim 52, further comprising mixing the adhesive or sealant material with a second material prior to dispensing the adhesive or sealant material from the applicator/dispenser.

56. The method of claim 52, wherein the second material comprises at least one of a medicament, a polymerization initiator, a polymerization rate modifier and a stabilizer for a polymerizable monomer.

57. The applicator/dispenser according to claim 1, wherein the actuator is movably attached to the body portion at a pivot point at a rear end of the body portion.

58. The applicator/dispenser according to claim 1, wherein the mixing chamber is housed within the body portion.

59. The applicator/dispenser according to claim 1, wherein the mixing chamber is external of the body portion.

60. The applicator/dispenser according to claim 1, further comprising a second container disposed at least partially located in the bladder, wherein movement of the actuator relative to the body portion moves the piercing or breaking portion without breaking the second container.

61. The applicator/dispenser according to claim 60, further comprising a container of adhesive or sealant material at least partially disposed within the second container and at least partially located in the cavity, wherein movement of the actuator relative to the body portion moves the piercing or breaking portion to rupture the container without breaking the second container.

* * * * *